US008454658B2

(12) United States Patent
Lindner

(10) Patent No.: US 8,454,658 B2
(45) Date of Patent: Jun. 4, 2013

(54) SURGICAL BONE ANCHORING DEVICE AND SPINAL COLUMN FIXATION SYSTEM

(75) Inventor: Stephan Lindner, Wurmlingen (DE)

(73) Assignee: Aesculap AG, Tuttlingen (DE)

( * ) Notice: Subject to any disclaimer, the term of this patent is extended or adjusted under 35 U.S.C. 154(b) by 239 days.

(21) Appl. No.: 12/822,494

(22) Filed: Jun. 24, 2010

(65) Prior Publication Data
US 2010/0331897 A1    Dec. 30, 2010

(30) Foreign Application Priority Data

Jun. 26, 2009  (DE) .......................... 10 2009 032 034

(51) Int. Cl.
*A61B 17/70*    (2006.01)
(52) U.S. Cl.
USPC .......................................... 606/246; 606/305
(58) Field of Classification Search
USPC ............. 606/70–71, 246, 250–261, 264–275, 606/280–299, 305–308; 411/2–5, 910
See application file for complete search history.

(56) References Cited

U.S. PATENT DOCUMENTS

| 719,161 | A |   | 1/1903 | Stuphen |
|---|---|---|---|---|
| 4,408,936 | A | * | 10/1983 | Williamson ...................... 411/3 |
| 5,443,467 | A |   | 8/1995 | Biedermann et al. |
| 5,484,437 | A |   | 1/1996 | Michelson |
| 5,499,892 | A |   | 3/1996 | Reed |
| 5,534,001 | A |   | 7/1996 | Schlapfer et al. |
| 5,550,146 | A |   | 8/1996 | Acosta et al. |
| 5,587,399 | A |   | 12/1996 | Acosta et al. |
| 5,653,710 | A |   | 8/1997 | Härle |
| 6,193,719 | B1 |   | 2/2001 | Gournay et al. |
| 6,299,616 | B1 | * | 10/2001 | Beger ........................... 606/86 R |
| 6,478,795 | B1 |   | 11/2002 | Gournay et al. |
| 2009/0062865 | A1 |   | 3/2009 | Schumacher |
| 2009/0069853 | A1 | * | 3/2009 | Schumacher ................. 606/301 |
| 2009/0076555 | A1 | * | 3/2009 | Lowry et al. ................... 606/280 |
| 2009/0105718 | A1 |   | 4/2009 | Zhang et al. |

FOREIGN PATENT DOCUMENTS

| DE | 79 01 696 U1 | 10/1979 |
|---|---|---|
| DE | 36 30 863 | 3/1988 |
| DE | 37 38 409 | 5/1989 |

(Continued)

OTHER PUBLICATIONS

European Search Report for corresponding European Application No. EP 10 16 7273 dated, Oct. 4 2010, with an English language EPO Form 1503 03.82 (P04C03), Nov. 30, 2010.

*Primary Examiner* — Todd Manahan
*Assistant Examiner* — Eric S Gibson
(74) *Attorney, Agent, or Firm* — RatnerPrestia

(57) ABSTRACT

A bone anchoring device for a spinal column fixation system includes an anchoring part, a bearing part for mounting at least one connection element thereon and a fixing element. The connection element is adapted for fixing to at least two bone anchoring devices. The anchoring part and the bearing part are mounted on each other, movable relative to each other in an assembly position and fixable relative to each other by the fixing element in an implantation position. The fixing element is of integral construction and has a proximal fixing element section, a distal fixing element section and a predetermined break-off area formed between the proximal and distal fixing element sections. The distal fixing element section has a receptacle for engagement with a tool for transferring the bone anchoring device from the assembly position to the implantation position. The device may be part of an improved spinal column fixation system.

21 Claims, 20 Drawing Sheets

FOREIGN PATENT DOCUMENTS

| | | |
|---|---|---|
| DE | 43 07 576 | 4/1994 |
| DE | 43 39 804 | 6/1995 |
| DE | 297 10 979 U1 | 2/1997 |
| DE | 198 51 370 | 9/2000 |
| DE | 693 31 528 | 10/2002 |
| DE | 695 27 608 | 2/2003 |
| DE | 20 2007 012 646 U1 | 12/2007 |
| DE | 20 2008 009 194 | 10/2008 |
| DE | 202008009194 U1 * | 10/2008 |
| DE | 10 2007 042 953 A1 | 3/2009 |
| GB | 203508 | 9/1923 |
| GB | 834787 | 5/1960 |
| WO | WO 94/26190 | 11/1994 |
| WO | WO 95/25487 | 9/1995 |
| WO | WO 96/29016 | 9/1996 |
| WO | WO 00/22997 | 4/2000 |
| WO | WO 2008/045719 | 4/2008 |

* cited by examiner

FIG.15
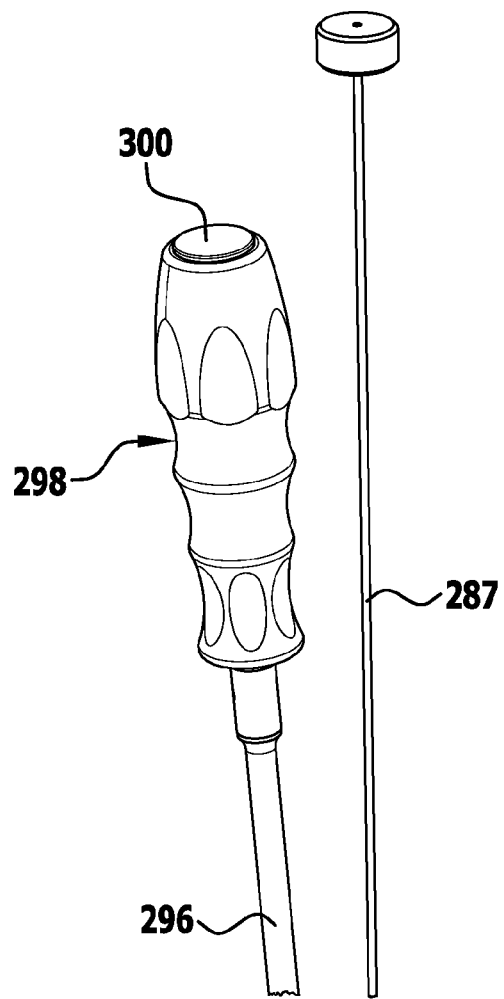
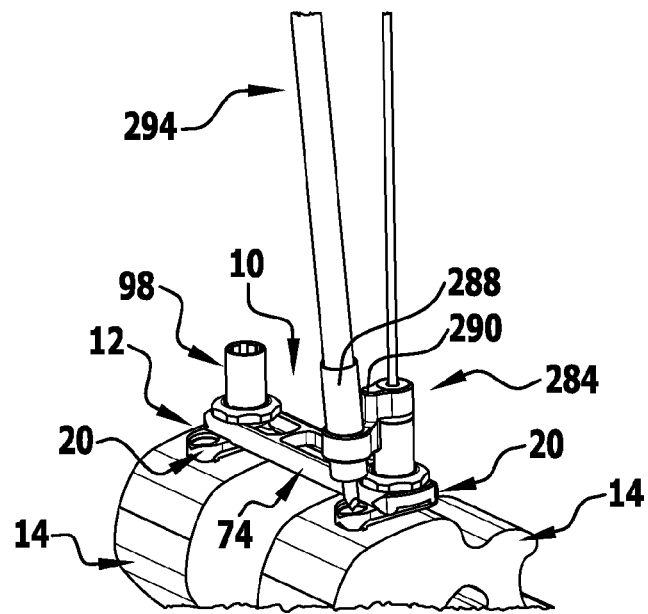

SURGICAL BONE ANCHORING DEVICE AND SPINAL COLUMN FIXATION SYSTEM

RELATED APPLICATIONS

This application claims priority under 35 U.S.C. §119 to German application number 10 2009 032 034.2 filed Jun. 26, 2009, the contents of which is incorporated herein by reference in its entirety and for all purposes.

FIELD OF THE INVENTION

The present invention relates to a surgical bone anchoring device generally, and more specifically to a surgical bone anchoring device for a spinal column fixation system. The present invention further relates to a spinal column fixation system generally, and more specifically to a spinal column fixation system comprising at least one surgical bone anchoring device.

BACKGROUND OF THE INVENTION

Surgical bone anchoring devices and also a spinal column fixation system are known, for example, from U.S. Pat. No. 6,299,616. In the known system it is, however, necessary to use a torque wrench to tension the fixing element with a defined holding torque against the anchoring part in order to fix the bearing part immovably on the anchoring part in the implantation position. A further development of such bone anchoring devices is known from US 2009/0105718 A1. The fixing element disclosed therein comprises a predetermined break-off area between a distal and a proximal fixing element section. It serves the purpose of dispensing with a torque wrench. Therefore, only a tool receptacle for a screwing-in tool is provided on the proximal fixing element section. When, upon tensioning the fixing element against the anchoring part, the fracture torque specified by the predetermined break-off area is exceeded, the fixing element shears off between the distal and proximal fixing element sections. The distal fixing element section then holds the bearing part with a holding torque corresponding to the shear-off torque of the predetermined break-off area in a clamped manner on the anchoring part.

On the basis of the above prior art, the problem does, however, arise during a surgical procedure that it is very awkward to move the fixing element up to the bearing part and connect, in particular, screw the fixing element to the bearing part in order to tension the bearing part against the anchoring part. It is known to temporarily connect long guide sleeves to the bearing part in order to facilitate insertion of the fixing element and tools required for this. However, the connecting of guide sleeves to the bearing part is not very easy, particularly not when the view of the parts to be connected to one another is impeded and therefore requires great manual dexterity on the part of the surgeon. In addition, each surgical step involves more time.

Therefore, it would be desirable to provide an improved surgical bone anchoring device and an improved spinal column fixation system of the kind described at the outset that simplify a surgical procedure, in particular, the stabilization of a spinal column.

SUMMARY OF THE INVENTION

The present invention relates to a surgical bone anchoring device for a spinal column fixation system, comprising an anchoring part adapted for anchoring in or on a bone, a bearing part adapted for mounting of at least one connection element thereon, the connection element being adapted for fixing to at least two bone anchoring devices of the spinal column fixation system, and a fixing element, wherein the anchoring part and the bearing part are mounted on each other, movable relative to each other in an assembly position and fixable relative to each other by the fixing element in an implantation position, the fixing element being of integral construction and having a proximal fixing element section, a distal fixing element section and a predetermined break-off area formed between the proximal and distal fixing element sections.

The present invention further relates to a spinal column fixation system, comprising at least one surgical bone anchoring device, comprising an anchoring part adapted for anchoring in or on a bone, a bearing part adapted for mounting of at least one connection element thereon, the connection element being adapted for fixing to at least two bone anchoring devices of the spinal column fixation system, and a fixing element, wherein the anchoring part and the bearing part are mounted on each other, movable relative to each other in an assembly position and fixable relative to each other by the fixing, element in an implantation position, the fixing element being of integral construction and having a proximal fixing element section, a distal fixing element section and a predetermined break-off area formed between the proximal and distal fixing element sections.

In a first aspect of the invention, a surgical bone anchoring device for a spinal column fixation system comprises an anchoring part adapted for anchoring in or on a bone, a bearing part adapted for mounting of at least one connection element thereon and a fixing element. The connection element is adapted for fixing to at least two bone anchoring devices of the spinal column fixation system. The anchoring part and the bearing part are mounted on each other, movable relative to each other in an assembly position and fixable relative to each other by the fixing element in an implantation position. The fixing element is of integral construction and has a proximal fixing element section, a distal fixing element section and a predetermined break-off area formed between the proximal and distal fixing element sections. And the distal fixing element section has provided thereon a tool element receptacle for engagement by force locking and/or positive locking with a tool for transferring the bone anchoring device from the assembly position to the implantation position.

In a second aspect of the invention a spinal column fixation system comprises at least one surgical bone anchoring device. The at least one surgical bone anchoring device comprises an anchoring part adapted for anchoring in or on a bone, a bearing part adapted for mounting of at least one connection element thereon, and a fixing element. The connection element is adapted for fixing to at least two bone anchoring devices of the spinal column fixation system. The anchoring part and the bearing part are mounted on each other, movable relative to each other in an assembly position and fixable relative to each other by the fixing element in an implantation position. The fixing element is of integral construction and has a proximal fixing element section, a distal fixing element section and a predetermined break-off area formed between the proximal and distal fixing element sections. And the distal fixing element section has provided thereon a tool element receptacle for engagement by force locking and/or positive locking with a tool for transferring the bone anchoring device from the assembly position to the implantation position.

BRIEF DESCRIPTION OF THE DRAWING FIGURES

The foregoing summary and the following description may be better understood in conjunction with the drawing figures, of which:

FIG. 15 shows a perspective view in analogy with FIG. 14 with a targeting device placed on a centering element of a bone anchoring device;

DETAILED DESCRIPTION OF PREFERRED EMBODIMENTS OF THE INVENTION

Figure 1:
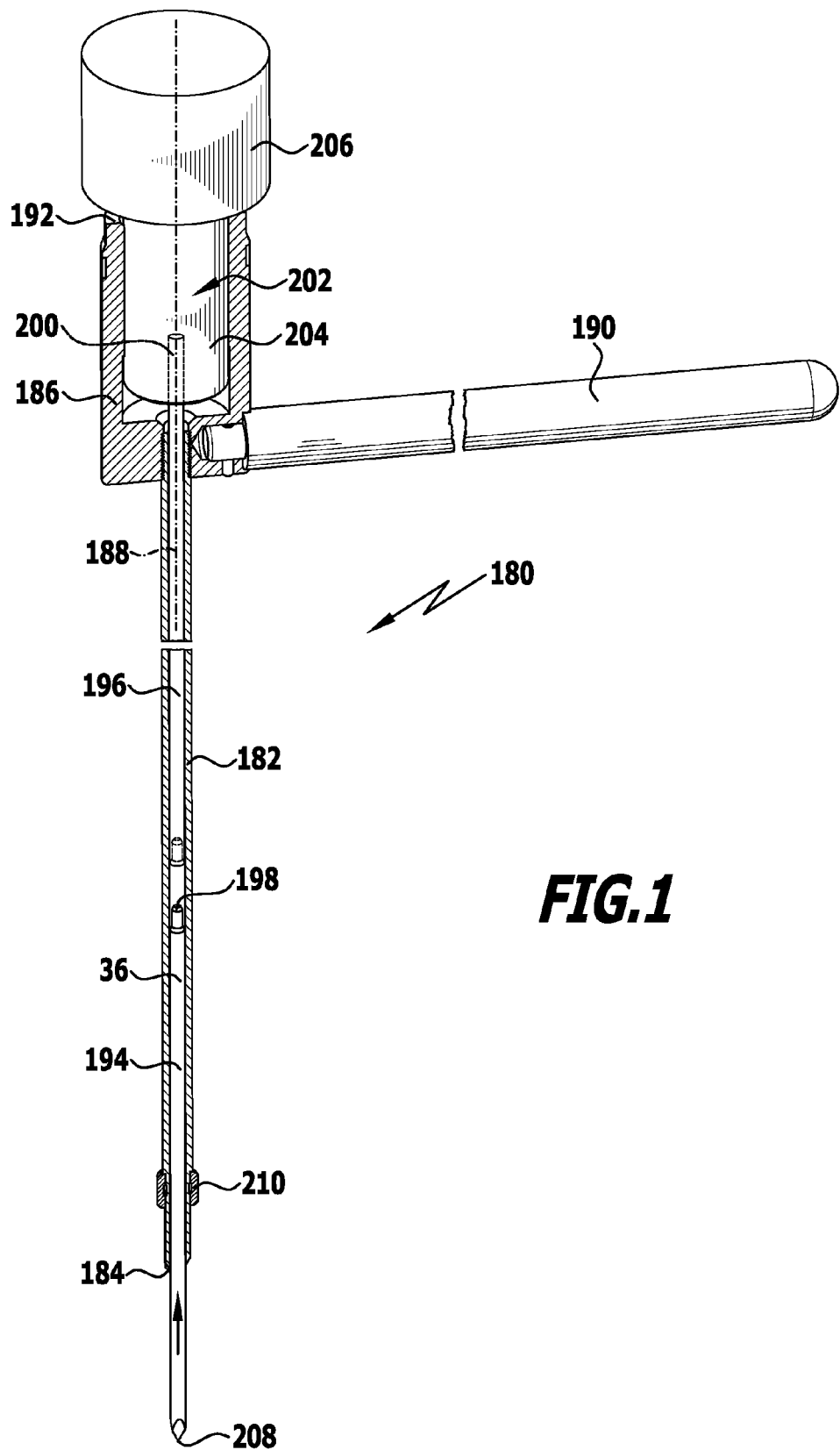
FIG. 1 shows a partly sectional view through an instrument for the application of a K-wire.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a surgical bone anchoring device for a spinal column fixation system, comprising:
an anchoring part adapted for anchoring in or on a bone;
a bearing part adapted for mounting of at least one connection element thereon, said connection element being adapted for fixing to at least two bone anchoring devices of the spinal column fixation system; and
a fixing element;
wherein said anchoring part and said bearing part are mounted on each other, movable relative to each other in an assembly position and fixable relative to each other by the fixing element in an implantation position, said fixing element being of integral construction and having a proximal fixing element section, a distal fixing element section and a predetermined break-off area formed between the proximal and distal fixing element sections, and the distal fixing element section having provided thereon a tool element receptacle for engagement by force locking and/or positive locking with a tool for transferring the bone anchoring device from the assembly position to the implantation position.

Moreover, the present invention relates to a spinal column fixation system comprising at least one surgical bone anchoring device, said at least one surgical bone anchoring device comprising:
an anchoring part adapted for anchoring in or on a bone;
a bearing part adapted for mounting of at least one connection element thereon, said connection element being adapted for fixing to at least two bone anchoring devices of the spinal column fixation system; and
a fixing element;
wherein said anchoring part and said bearing part are mounted on each other, movable relative to each other in an assembly position and fixable relative to each other by the fixing element in an implantation position, said fixing element being of integral construction and having a proximal fixing element section, a distal fixing element section and a predetermined break-off area formed between the proximal and distal fixing element sections, and the distal fixing element section having provided thereon a tool element receptacle for engagement by force locking and/or positive locking with a tool for transferring the bone anchoring device from the assembly position to the implantation position.

The further development of known bone anchoring devices and spinal column fixation systems by the proposed configuration of the fixing element makes it possible to connect, in particular, a centering element to the bearing part by means of the fixing element, prior to insertion in a patient's body, i.e., to preassemble the bone anchoring device in such a way that the fixing element is already connected to the bearing part. After fixing the anchoring part to a bone and aligning the bearing part relative to the anchoring part, there is then no longer any need to connect the fixing element to the bearing part. Therefore, this assembly step does not have to be carried out during the surgical procedure, but instead can already take place during assembly of the bone anchoring device, in particular, directly during manufacture thereof or prior to performing a surgical procedure. By providing the tool element receptacle preferably solely on the distal fixing element section, a surgeon has the possibility of individually specifying a holding torque which he can apply, for example, with a torque wrench provided for this. Furthermore, by providing a centering element held by the fixing element on the bearing part, for example, it is possible to prevent loss of the proximal fixing element section in or at the surgical site after the predetermined break-off area has been destroyed. In particular, it is then conceivable to remove the proximal fixing element section together with the centering element from the surgical site.

The bone anchoring device expediently comprises a centering element which is held by the fixing element on the bearing part. The centering element makes it possible, in a simple and safe way, to move further instruments and, if required, holding, clamping or tensioning elements of the bone anchoring device or of the spinal column fixation system up to the bone anchoring device. There is no need for the centering element to be connected to and, if required, released from the bearing part in a complicated manner during the surgical procedure, which enables the operating time to be significantly shortened. Nor is there any need, for example, for the centering element to be screwed to the bearing part when the fixing element tensions or holds the centering element appropriately against the bearing part. This also allows the anchoring device to be preassembled in such a way that the fixing element provided for fixing the bearing part on the anchoring part can already be preassembled on the bone anchoring device and, at the same time, it serves the purpose of temporarily holding the centering element on the bearing part. It is thus also possible to so construct the centering element and the fixing element that the predetermined break-off area can be severed by acting upon the fixing element, in particular, its distal fixing element section, with a tensile force and torque. The centering element is preferably held immovably on the bearing part by the fixing element.

The design of the centering element is particularly simple when it is in the form of a centering sleeve. The centering sleeve makes it possible to move parts through it and over the outside of it up to the bone anchoring device, in particular, to its bearing part.

The surgical bone anchoring device advantageously comprises a positioning device for positioning the centering element and the bearing part relative to each other in the assembly position. In particular, the positioning device makes it possible to hold the centering element in a defined manner by means of the fixing element on the bearing part.

The design of the positioning device is particularly simple when it comprises first and second positioning members which are arranged or formed, on the one hand, on the centering element and, on the other hand, on the bearing part, and when the first and second positioning members engage one another by force locking and/or positive locking in the assembly position. In particular, the positioning device may be so configured that the first and second positioning members form a protection against rotation so that, for example, the centering element is prevented from rotating about a longitudinal axis defined by it relative to the bearing part. This allows the centering element to be held by the fixing element in a defined manner on the bearing part, for example, for the centering element to be tensioned against the bearing part. Apart from the positioning device, there is then no need for any further connecting elements for holding the centering element on the bearing part. In particular, the fixing element alone can be used for this.

The design of the positioning device can be further simplified when a first positioning member is in the form of a positioning projection, and when a second positioning member is in the form of a positioning receptacle corresponding to the positioning projection. The positioning projection and the positioning receptacle may be selectively arranged or formed on the centering element or on the bearing part.

The first and second positioning members can be made to engage in a simple way when they face in a direction parallel or substantially parallel to a longitudinal axis of the centering element.

The fixing element expediently holds the centering element immovably on the bearing part in the assembly position. This allows a particularly good guidance of further implant parts or of instruments of an instrumentation used for the implantation by the centering element.

It is advantageous for the fixing element to hold the centering element by force locking and/or positive locking on the bearing part in the assembly position. The centering element can be held particularly simply on the bearing part when the fixing element tensions the centering element against the bearing part in the assembly position.

It may also prove expedient for the fixing element to hold the centering element clamped on the bearing part in the assembly position. In particular, it is thus possible for a part or a section of the centering element to be held clamped between a corresponding section of the fixing element and the bearing part in the assembly position.

In accordance with a further preferred embodiment of the invention, a coupling device may also be provided for coupling the centering element and the fixing element. In particular, the coupling device may enable movable or immovable coupling of the centering element and the fixing element relative to each other. Also, the coupling device has the advantage that after destruction of the predetermined break-off area, in particular, the proximal fixing element section and the centering element may continue to be coupled to each other, more specifically, in such a way that relative movement between the centering element and the proximal fixing element section may or may not be enabled.

The coupling device preferably comprises first and second coupling members, which are arranged, on the one hand, on the centering element and, on the other hand, on the fixing element, the first and second coupling members engaging one another in a coupling position in which the bone anchoring device assumes the assembly position. In particular, engage one another may also mean that the coupling members bear on one another and thereby effect a coupling between the centering element and the fixing element. In particular, the coupling members may be in the form of stops, which restrict a relative movement of the centering element and the fixing element parallel or substantially parallel to a longitudinal axis defined by the centering element. In particular, a stop may be provided on the fixing element, which prevents movement of the centering element in the proximal direction away from the fixing element, and, optionally, also away from the bearing part.

The design of the coupling device is particularly simple when a first coupling member is in the form of a first stop surface facing in the proximal direction on the centering element, when a corresponding second coupling member is in the form of a second stop surface facing in the distal direction on the fixing element, and when the first and second stop surfaces bear on each other in the coupling position. Such a coupling device makes it possible for the centering element to be tensioned against the bearing part by the fixing element, in particular, without the centering element having to be rotated relative to the bearing part. In particular, there is therefore no need for the centering element to be screwed to the bearing part, which makes particularly slim designs of both the bearing part and the centering element possible. In particular, it is possible to pull the centering element against the bearing part and hold it under tension with the fixing element. Furthermore, the coupling members also optionally form abutments which may be used to withstand the tensile and/or torsional forces required to destroy the predetermined break-off area. If, for example, the fixing element, starting from the assembly position in which it holds the centering element on the bearing part, is moved further in the distal direction, then the coupling members can absorb the additionally occurring torsional and tensile forces. If, however, these exceed the break values of the predetermined break-off area, it is destroyed, and the distal fixing element section is severed from the proximal fixing element section. The proximal fixing element section, as it is still coupled to the centering element by the coupling device, can then be simply and safely removed from the surgical site. The distal fixing element section can then be used to transfer the bone anchoring device to the implantation position in which the bearing part and the anchoring part can no longer move relative to each other.

The positioning device and the coupling device expediently secure the centering element in the assembly position and in the coupling position on the bearing part so that the centering element is unable to rotate about a longitudinal axis defined by the centering element. This allows a defined positioning of the centering element and the bearing part relative to each other.

In accordance with a further preferred embodiment of the invention, it may be provided that the fixing element has a fixing surface which, in the implantation position, bears on a fixing surface area of the anchoring part, and that the fixing surface is spaced from the fixing surface area when the coupling device assumes the coupling position and so long as the distal and proximal fixing element sections are connected to each other via the predetermined break-off area. This design of the bone anchoring device ensures that the bearing part and the anchoring part can only be immovably fixed to each other when the predetermined break-off area is destroyed. So long as the fixing element is undamaged, it is therefore not possible to move the fixing surface up to the fixing surface area. Owing to the special design and arrangement of the coupling device, this requires the predetermined break-off area to be destroyed. Accordingly, if the bone anchoring device is to be transferred to the implantation position, the predetermined break-off area must be destroyed, which causes the two fixing element sections to be severed from each other. The distal fixing element section then serves to immovably fix the bearing part on the anchoring part, and the proximal fixing element section used to hold the centering element on the bearing part can be simply and safely removed with the aid of the centering element from the surgical site. With the improved bone anchoring device, it is therefore possible, in a single operational step, to immovably fix the bearing part and the anchoring part relative to each other and to separate the centering element from the bearing part and remove it.

It is advantageous for the bearing part and the anchoring part to be movable relative to each other when the predetermined break-off area is undamaged. In other words, this means that the bearing part and the anchoring part are movable relative to each other and, consequently, adjustable so long as the centering element is held on the bearing part by the fixing element. Only when all of the parts of the bone anchoring device or the spinal column fixation system are arranged and fixed in the body, can the relative position of the bearing part and the anchoring part that is intended by the surgeon be permanently fixed, by means of the fixing element, and the centering element removed in the described manner.

To ensure that fixing elements that have been used once cannot be used repeatedly, it is expedient for the distal and proximal fixing element sections to be irreversibly separable from each other by destroying the predetermined break-off area.

In accordance with a further preferred embodiment of the invention, it may be provided that the predetermined break-off area is formed by a weakening of the fixing element between the distal and proximal fixing element sections.

For example, a wall thickness of the fixing element can be reduced to form the predetermined break-off area. This can be produced by, for example, a recess in an outer wall surface of a sleeve-shaped fixing element.

It is particularly easy to secure the fixing element to the bearing part when these are adapted to be screwed to each other. In addition, the clamping forces required for permanently clamping the bearing part and the anchoring part can thus be reliably applied.

It is advantageous for the fixing element to have an external thread section and for the bearing part to have a corresponding internal thread section. This allows the fixing element to be screwed into the interior of, for example, a sleeve-shaped section of the bearing part and to secure a head portion of an anchoring element arranged therein in a clamped manner in the implantation position.

In principle, it is conceivable to form the external thread section on the proximal fixing element section. It is, however, more expedient for the external thread section to be formed on the distal fixing element section. In cooperation with a screwing-in tool, which engages the tool element receptacle formed on the distal fixing element section, the distal fixing element section can thus be used in the desired manner, i.e., like a conventional fixing screw, to be tensioned, at the end of the surgical procedure, against, for example, a head portion of the anchoring part held on or in the bearing part.

The fixing element can be of particularly compact design when the predetermined break-off area borders proximally on the external thread section. In particular, it can thereby be ensured that only the section of the fixing element that actually serves to fix the bone anchoring device in the implantation position ultimately remains in the patient's body.

To facilitate assembly of the centering element by means of the fixing element on the bearing part, it is expedient for the proximal fixing element section to have a larger outer diameter than the distal fixing element section. In particular, this makes it possible to pass the distal fixing element section from the proximal end through the centering element in such a way that the distal fixing element section projects distally over the centering element and is engageable with, in particular, screwable to, the bearing part.

The fixing element is preferably of sleeve-shaped design. The sleeve-shaped design makes it possible to access, for example, with a tool a proximal end of the anchoring part through the fixing element in order, for example, to drive, for example, screw, the anchoring part further into a bone or to move it out of the bone again.

The tool element receptacle is advantageously constructed with multiple inner edges or multiple inner rounded surfaces. Screwing-in tools constructed with multiple outer edges or multiple outer rounded surfaces, which are usually available, can thus be used for engagement with the fixing element.

In order that the anchoring part can be introduced into a bone in a simple way, for example, screwed in, it is advantageous for the anchoring part to comprise a tool receptacle which is open and faces in the proximal direction.

Conventional screwing-in tools can be used to introduce the anchoring part into a bone when the tool receptacle has multiple inner edges or multiple inner rounded surfaces.

In accordance with a further preferred embodiment of the invention, the bone anchoring device may comprise a clamping device for holding a connection element of the spinal column fixation system in a clamped manner on the bearing part. In particular, the connection element may be fixed to two bone anchoring devices in order to fix, for example, two vertebrae at a spacing from each other specified by the surgeon.

The bone anchoring device is particularly easy to handle when the clamping device comprises at least one connection element receptacle for receiving a connection element or a part thereof, and an external thread on the bearing part, and a nut with an internal thread corresponding to the external thread, with the nut at least partially reducing in size, in a clamping position, an insertion opening which opens up the connection element receptacle transversely to a longitudinal axis defined by the connection element receptacle. With such a clamping device, a connection element inserted at least partially or in sections into the connection element receptacle can be held clamped by the nut in the clamping position.

To optimize clamping of the connection element in the connection element receptacle, it is advantageous for a longitudinal axis of the connection element receptacle and a longitudinal axis of the centering element to extend in a skew manner in relation to each other in the assembly position. In particular, skew may mean that planes extending perpendicularly to the two longitudinal axes intersect each other perpendicularly and, in particular, contain the respective other longitudinal axis or at least extend parallel thereto.

It may also prove advantageous for the bone anchoring device to comprise a securing device for securing the proximal fixing element section on the centering element after separation of the distal and proximal fixing element sections from each other. In particular, with the securing device, the proximal fixing element section separated from the distal fixing element section can be prevented from becoming unintentionally detached from the centering element and getting lost.

The design of the securing device is particularly simple when it comprises an internal toothing on the centering element proximally of the coupling member provided on the centering element, and a corresponding external toothing of the proximal fixing element section. This makes it possible to introduce the proximal fixing element section from the proximal end into the centering element, with the toothings, during assembly of the fixing element on the centering element, allowing over a length defined by them only movement of the fixing element parallel to the longitudinal axis of the centering element and only rotation about the longitudinal axis again when the toothings are out of engagement. Only a slight rotation is then sufficient to prevent movement of the fixing element in the proximal direction again. The internal toothing of the centering element then forms a stop for the proximal fixing element section, thereby preventing movement of the fixing element in the proximal direction. In particular, the proximal fixing element section can thereby be secured between the internal toothing and one of the two coupling members of the coupling device that is arranged on the centering element, in order to prevent detachment of the proximal fixing element section from the centering element.

To enable introduction of the fixing element from the proximal end through the centering element, it is advantageous for a maximum inner diameter of the internal toothing in the area of a tooth base to be equal to or greater than a maximum outer diameter of the external toothing.

To form a stop for preventing movement of the fixing element in the proximal direction, it is advantageous for a minimum inner diameter of the internal toothing to be smaller than a maximum outer diameter of the external toothing.

In accordance with a further preferred embodiment of the invention, it may be provided that the bearing part comprises at least one fastening element receptacle for a fastening element which is fixable to a bone. In particular, the fastening element may be provided in addition to the anchoring part, which in this respect also forms a fastening element.

The bearing part and the anchoring part are preferably pivotable relative to each other in the assembly position. Angles specified by a surgeon between longitudinal axes of the bearing part and the anchoring part can thus be set during the surgical procedure and, if need be, fixed by the fixing element.

A surgeon is particularly flexible in terms of adjustment when the bearing part and the anchoring part are mounted on each other in the manner of a ball-and-socket joint in the assembly position. For example, in order to form a ball-and-socket joint, the anchoring part may have a spherical proximal end which corresponds constructionally to a hollow dome-shaped seat provided on the bearing part.

The bearing part and the anchoring part can be fixed to each other particularly easily and reliably in the implantation position when the fixing element is in the form of a clamping element for holding in a clamped manner a head section of the anchoring part in a seat of the bearing part for the head section.

The bone anchoring device can be easily and reliably anchored to a bone when the anchoring part is in the form of a screw body with an external thread. The external thread is preferably in the form of a bone thread.

Alternatively, it is, of course, also conceivable for the anchoring part to be in the form of a hook, in particular, in the form of a bone hook, which can be driven into a bone.

It is expedient for at least one bone anchoring device of the spinal column fixation system to be in the form of one of the bone anchoring devices described above. The spinal column fixation system in its entirety then has the advantages described above in conjunction with preferred embodiments of the bone anchoring devices.

The spinal column fixation system expediently comprises at least two bone anchoring devices. In particular, these can be fixed to two adjacent vertebrae, so that the two vertebrae can be fixed at a defined spacing from each other by a connection element which is fixable to the bone anchoring devices.

It is advantageous for the spinal column fixation system to comprise at least one connection element which is fixable to two bone anchoring devices. For example, two vertebrae can thereby be fixed at a predefined spacing from each other by the spinal column fixation system in the described manner.

The design of the spinal column fixation system is particularly simple when the at least one connection element is rod-shaped or has a rod-shaped or ring-shaped connection section. In particular, the connection element is preferably constructed in such a way that it can be inserted partially into a corresponding connection element receptacle on the bone anchoring device, in particular, on the bearing part, and fixed in a clamped manner by a clamping device provided for this purpose.

A spinal column fixation system generally denoted by reference numeral 10, comprising two bone anchoring devices 12, is diagrammatically represented in FIGS. 1 to 20. It serves to fix two adjacent vertebrae 14, for example, which are diagrammatically represented in the Figures, relative to each other, in order, for example, to thereby relieve an intervertebral disc space 16 defined between the vertebrae 14. The elements which the spinal column fixation system 10 comprises and the instruments used to implant it will be explained hereinbelow in detail with reference to the Figures.

The bone anchoring device 12 comprises an anchoring part 18 and a bearing part 20. The anchoring part 18 is in the form of a bone screw 24 defining a longitudinal axis 22. The bone screw 24 comprises an elongate screw shaft 26 tapering conically to some extent in the distal direction, which has an external thread 28 in the form of a bone thread. Optionally, the external thread 28 may be of self-cutting design. A proximal end of the bone screw 24 is formed by a screw head 30 defining a head section. The screw head 30 defines a maximum outer diameter which is greater than a maximum outer diameter of the external thread 28. The screw head 30 is also provided with an external thread 32. Optionally, the screw shaft 26 may be cannulated. This means that it has a longitudinal bore 34 extending coaxially with the longitudinal axis 22. As will be explained in further detail hereinbelow, the longitudinal bore 34 serves to receive a K-wire 36 in order to fix the bone screw in a defined manner on a vertebra 14. A short, thread-free, cylindrical shaft section 38 extends between the external thread 32 and the screw head 30. A tool receptacle 40 extending coaxially with the longitudinal axis 22 and open so as to face in the proximal direction is formed on the screw head 30. The tool receptacle 40 may be selectively constructed with multiple inner edges or multiple inner rounded surfaces; in particular, it may be in the form of a Torx® socket.

The bearing part 20 comprises a substantially plate-shaped main body 42 having on an underside 44 two surface areas 46 and 47 which are inclined at a few degrees to each other. There is formed in the main body 42 a hollow dome-shaped seat 48 for the screw head 30, whose inner diameter is adapted to the outer diameter of the screw head 30. The seat 48 is open towards the underside 44 by way of a through-bore 50. An inner diameter of the through-bore 50 is selectively somewhat larger than a maximum outer diameter of the external thread 28 or at least of such dimensions that the screw shaft 26, if its external thread 28 is somewhat larger in outer diameter than the through-bore 50 can be screwed through the latter.

At the proximal end, the seat 48 is adjoined by a short sleeve section 52 projecting in the proximal direction, which has an internal thread 54 and an external thread 56. The internal thread 54 corresponds to the external thread 32 of the screw head 30, so that the screw head 30, which has a larger outer diameter than a free inner diameter of the sleeve section 52 in the area of the internal thread 54 can be screwed in through the latter coaxially with a longitudinal axis 58 defined by the sleeve section 52. The longitudinal axis 58 extends perpendicularly to the surface area 47. After the bone screw 24 has been screwed in with its screw head 30 through the sleeve section 52, the screw head 30 is held movably in the seat 48. A ball-and-socket joint 60 is thereby formed between the bone screw 24 and the bearing part 20. Such an assembly is also known in the literature by the term "polyaxial screw", as the bearing part 20, owing to the ball-and-socket joint 60, can be polyaxially pivoted about a midpoint of the screw head 30 relative to the anchoring part 18.

There are machined in the main body 42, starting from its upper side 62, two connection element receptacles 64 and 66. The connection element receptacles 64 and 66 define at least in sections thereof hollow-cylindrical side surfaces 68 and 70 for receiving rod-shaped sections 72 of substantially circular cross section of a plate-shaped connection element 74 of the spinal column fixation system 10. Longitudinal axes 76 and 78 defined by the connection element receptacles 64 and 66 extend parallel to each other and each lie in a plane which perpendicularly intersects the longitudinal axis 58. In the area of the connection element receptacles 64 and 66, the external thread 56 is partially removed in each case. Furthermore, a transverse bore 80 extending transversely to the longitudinal axis 58 is provided in the area of the connection element receptacles 64 and 66 where the external thread 56 is partially removed.

A ring-shaped end face 82, facing in the proximal direction, of the sleeve section 52 is interrupted by two diametrically opposed cut-outs 84, which form first positioning members 86 of a positioning device generally denoted by reference numeral 88. The cut-outs 84 form in this way positioning receptacles for receiving in a positively locking manner second positioning members 90 in the form of corresponding positioning projections 92 which project from a ring-shaped end face 94, facing in the distal direction, of a centering element 98 in the form of a centering sleeve 96. The centering sleeve 96 has an outer diameter corresponding to a minimum outer diameter of the sleeve section 52 in the area of the external thread 56, so that a thread turn of the external thread 56 projects radially over a cylindrical outer surface defined by the centering sleeve 96.

The centering element 98 has, starting from its distal end defined by the end face 94, a short sleeve section 100, which defines a minimum inner diameter. The centering sleeve 96 widens proximally with one step adjoining the sleeve section 100, so that a ring-shaped stop surface 102 facing in the proximal direction is defined. Starting from the stop surface 102, a central sleeve section 104, which defines a maximum inner diameter of the centering sleeve 96, therefore extends in the proximal direction. A proximal sleeve section 106 adjoins the central sleeve section 104 proximally up to a proximal end 108 of the centering element 98. The sleeve section 106 is characterized by having an internal toothing 110 which is formed by a plurality of strip-shaped projections 112 extending parallel to the longitudinal axis 58 and projecting from an inside wall surface 114 approximately to the same extent as the width of the stop surface 102.

A fixing element generally denoted by reference numeral 116 is provided for fixing the centering element 98 in a defined manner by means of the positioning device 88 to the bearing part 20. The fixing element 116 is of integral construction and defines a distal fixing element section 118 and a proximal fixing element section 120 which are separated from each other by a predetermined break-off area 122.

The distal fixing element section 118 defines a ring-shaped, hollow dome-shaped fixing surface 124 facing in the distal direction, whose curvature matches the spherical outer contour of the screw head 30. The fixing surface 124 is proximally adjoined by a ring-shaped ring projection 126 facing in the direction towards the longitudinal axis 58 and defining a minimum inner diameter of the fixing element 116. Proximally of the ring projection 126, the fixing element 116 widens in the interior essentially with one step. Up to the predetermined break-off area 122, the distal fixing element section 118 is provided in the interior with a toothing 130 defining a tool element receptacle 128. The toothing 130 is constructed with multiple inner rounded surfaces, and, optionally, may be constructed with multiple inner edges. On its outer side, the fixing element 116 is provided with an external thread section 132, which corresponds constructionally to the internal thread 54 of the sleeve section 52. This makes it possible to screw the distal fixing element section 118 to the internal thread 54 of the sleeve section 52.

Starting from the predetermined break-off area 122, an inner diameter of the fixing element 116 widens in such a manner that it is completely free of toothing. The proximal fixing element section 120 is therefore not suited to engage with a screwing-in tool and thereby transmit a torque to the fixing element 116. Starting from a proximal end face 134, a ring flange 136 facing away from the longitudinal axis 58 in the radial direction is formed, which is provided with a plurality of grooves 138 for formation of an external toothing 140 which corresponds constructionally to the internal toothing 110. A maximum outer diameter of the external toothing 140 is slightly smaller than an inner diameter of the central sleeve section 104 and corresponds to a maximum inner diameter of the proximal sleeve section 106 in the area of a tooth base 142 of the internal toothing 110.

Figure 5:
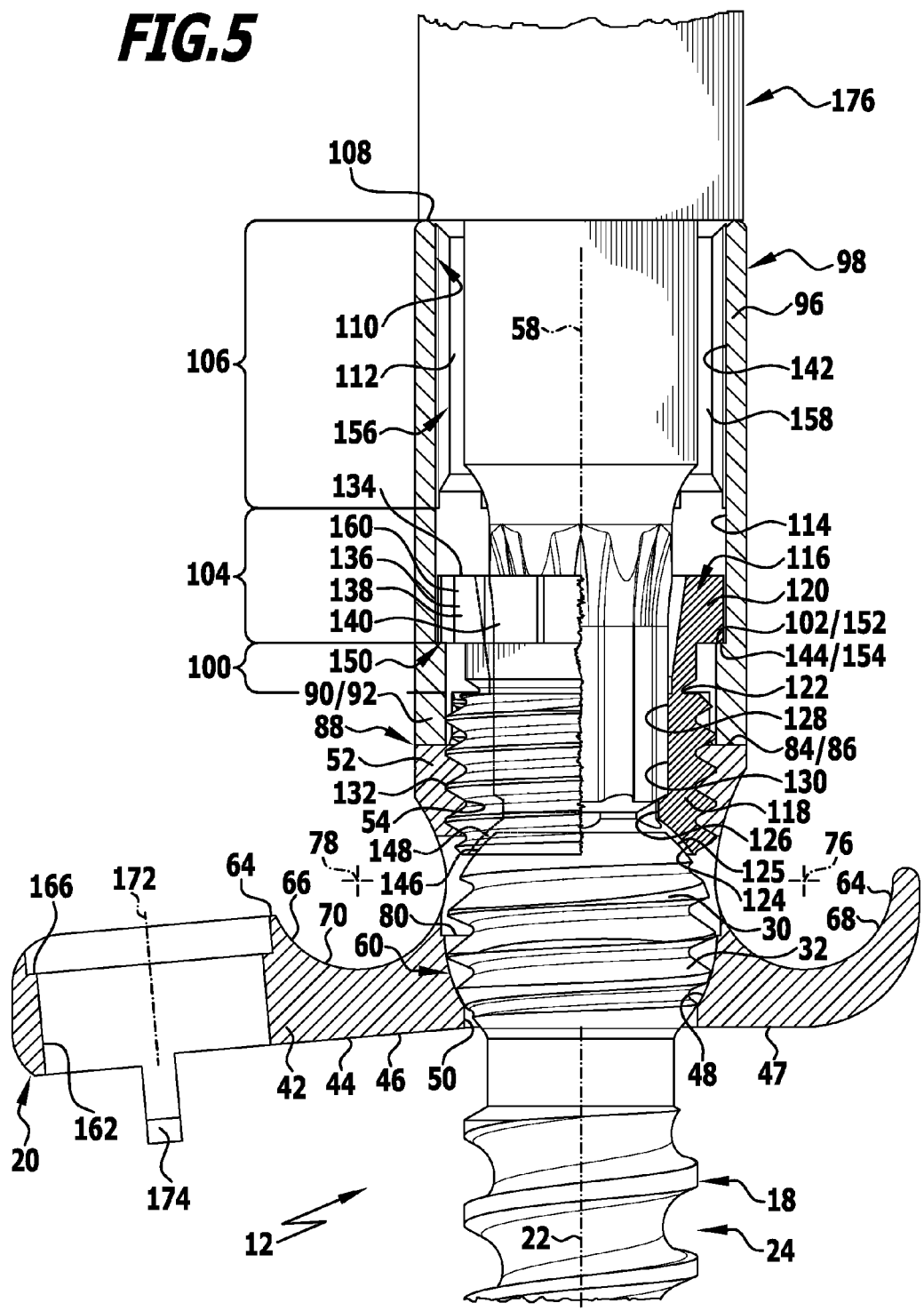
FIG. 5 shows a partly sectional view, in part, of the preassembled bone anchoring device from FIG. 4.
Figure 6:
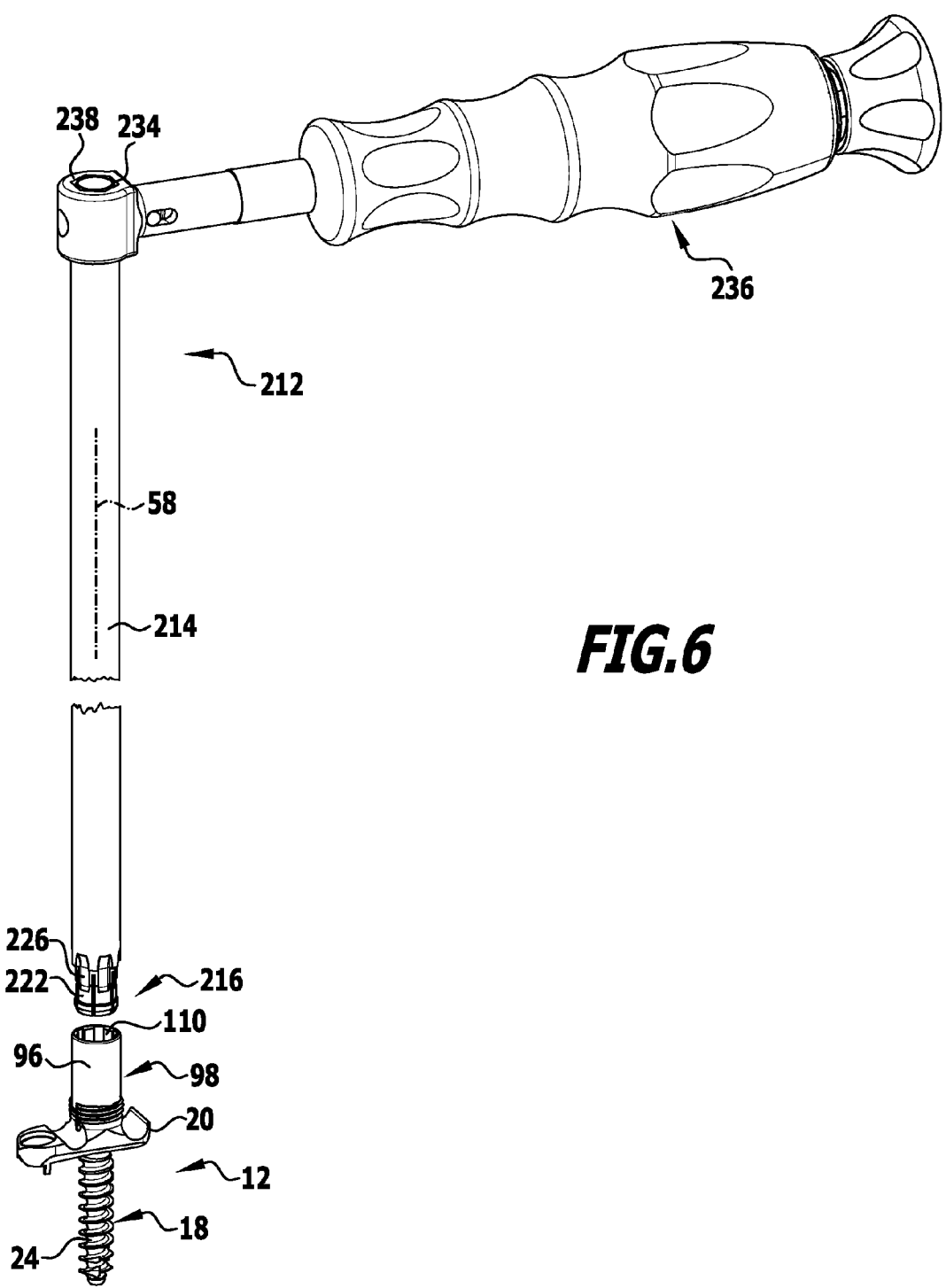
FIG. 6 shows a perspective, partly broken-open view of the bone anchoring device from FIG. 5 before connection to a holding and insertion instrument.
Figure 7:
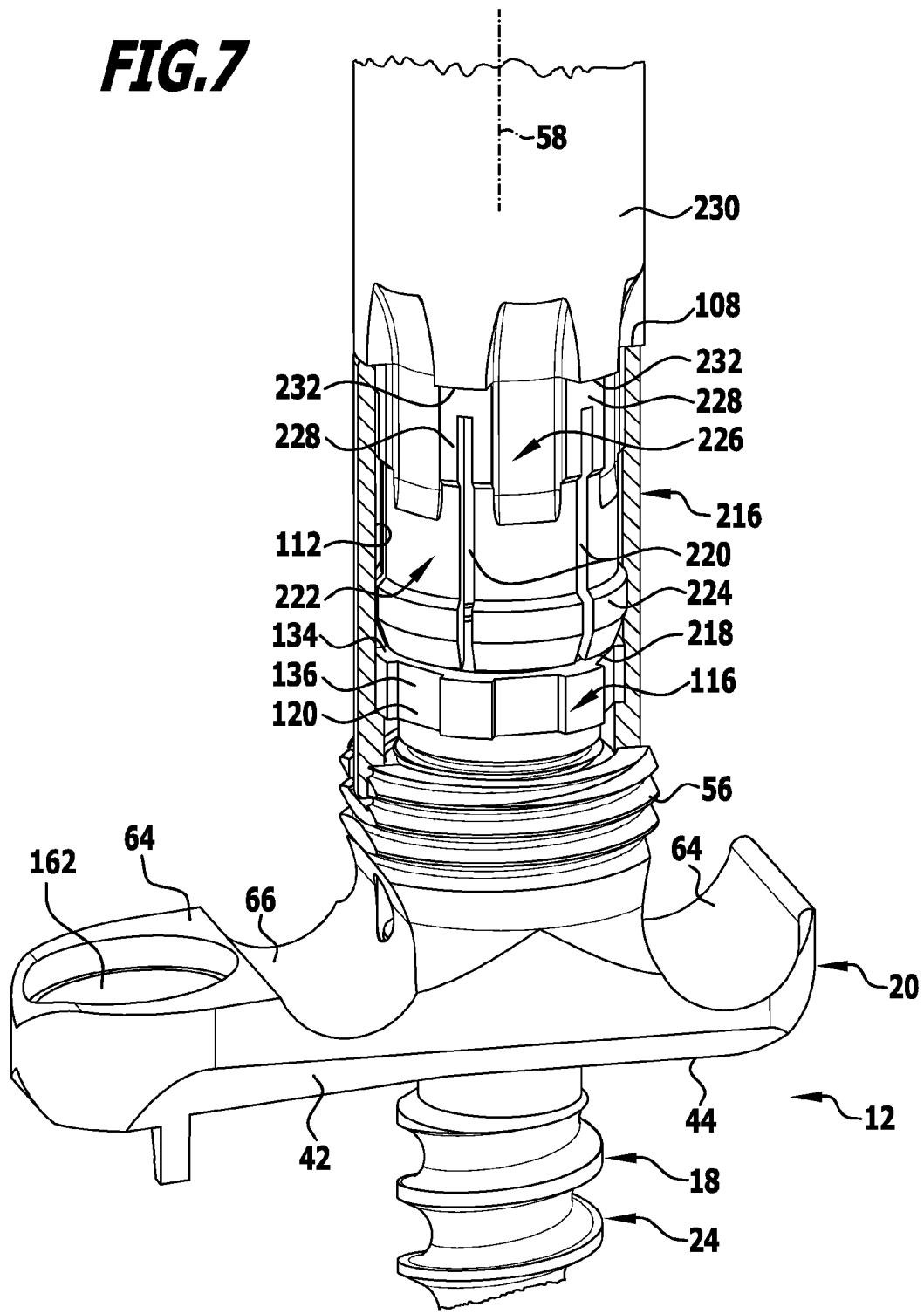
FIG. 7 shows a partly sectional, perspective view of the bone anchoring device with the holding and insertion instrument connected thereto.

The ring flange 136 defines a ring-shaped stop surface 144 facing in the distal direction, which in an assembly position of the bone anchoring device 12, as represented diagrammatically in FIG. 5, bears against the stop surface 102. The fixing element 116 is of such dimensions that in the assembly position the fixing surface 124 is spaced from a fixing surface area 146 of the screw head 30. The fixing surface area 146 is defined as the surface area of a surface of the screw head 30 on which the fixing surface 124 bears when the bearing part 20 and the anchoring part 18 are tensioned against each other and define an implantation position, as represented diagrammatically in FIG. 19. In the assembly position, the fixing surface 124 is spaced from the fixing surface area 146 by a gap 148.

The assembly position is defined by a coupling device generally denoted by reference numeral 150, which comprises a first coupling member 152 in the form of the stop surface 102 and a second coupling member 154 in the form of the stop surface 144. The first and second coupling members 152 and 154 bear against each other in a coupling position and are thereby in engagement with each other. They ensure that the fixing surface 124 is spaced from the fixing surface area 126 so long as the predetermined break-off area 122 is not damaged or destroyed. The coupling device 150 therefore simultaneously forms a movement delimiting device at least for the proximal fixing element section 120 in the distal direction. In the proximal direction, movement of the fixing element 116 is delimited by the end face 134 which strikes side surfaces, facing in the distal direction, of the projections 112 when the fixing element 116 is so rotated about the longitudinal axis 58 that the internal toothing 110 and the external toothing 140 cannot engage. In this way, the fixing element 116 is undetachably secured with its proximal fixing element section 120 on the centering element 98. In other words, the internal toothing 110 and the external toothing 140 form first and second securing members 158 and 160 of a securing device generally denoted by reference numeral 156 for securing the proximal fixing element section 120 on the centering element 98.

In the manner described, with the fixing element 116 and by engagement of the first and second positioning members 86 and 90, the centering element 98 can be tensioned against the bearing part 20 such that the end faces 94 and 82 bear on each other. Rotation of the centering element 98 about the longitudinal axis 58 relative to the bearing part 20 is then impossible.

Optionally, the main body 42 of the bearing part 20 may be of asymmetrical construction and additionally comprise adjacent to the connection element receptacle 66 a fastening element receptacle 162 in the form of a bore with an inner diameter tapering with one step in the distal direction. The bore serves to receive an additional fastening element 164 for securing the bearing part 20 in a rotationally locked manner on the vertebra 14. The one-stepped tapering of the inner diameter of the fastening element receptacle 162 defines a ring-shaped stop surface 166 facing in the proximal direction, which forms a stop for a ring flange 170 projecting radially from the head 168 of the fastening element 164. In particular, the fastening element 164 may be in the form of a bone screw, as represented diagrammatically in FIG. 17. A longitudinal axis 172 of the fastening element receptacle 162 extends perpendicularly to the surface area 46 and is therefore inclined at a few degrees to the longitudinal axis 58.

Figure 3:
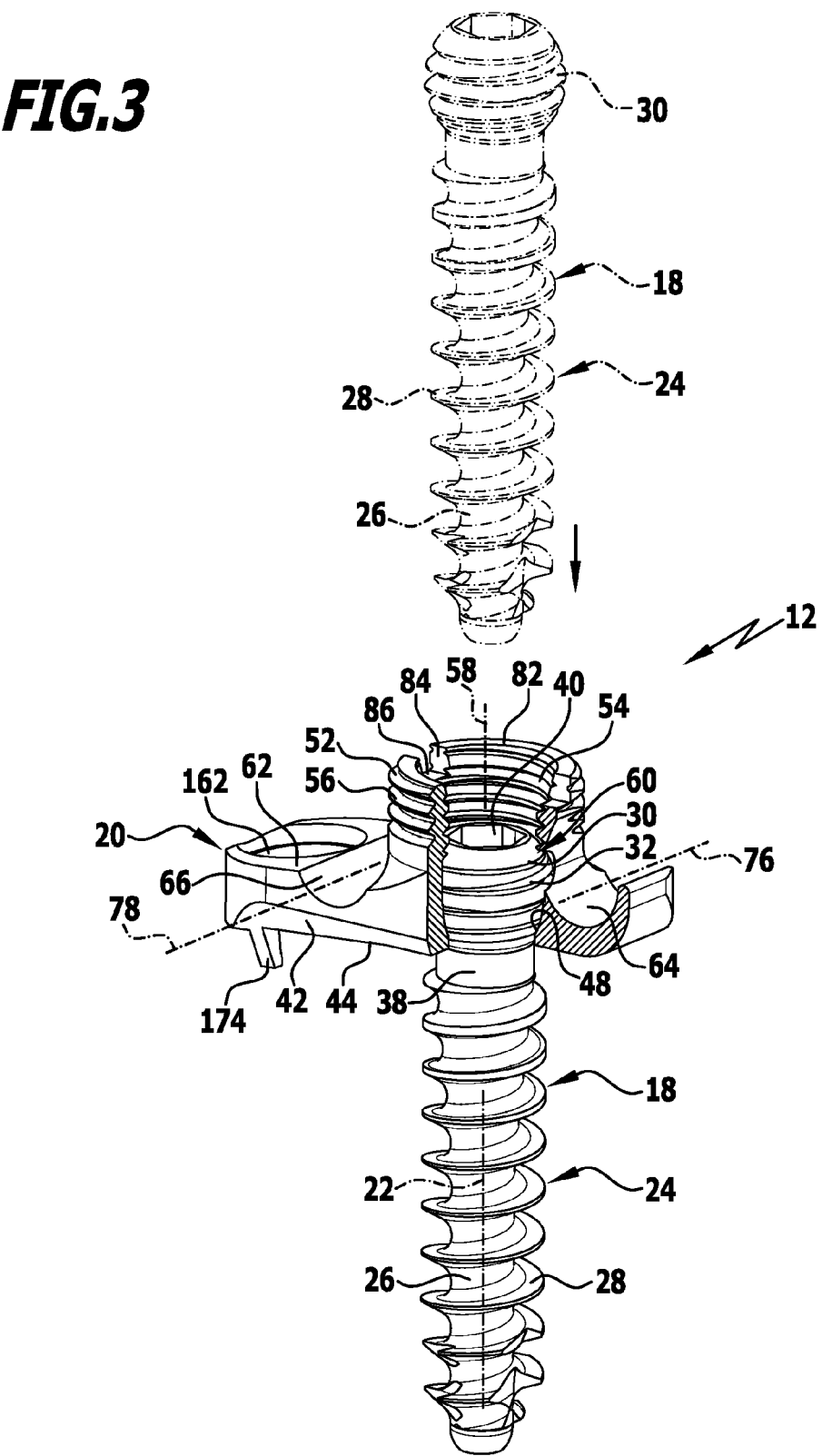
FIG. 3 shows a diagrammatic representation of part of a bone anchoring device during assembly of its bearing part and anchoring part on each other.
Figure 4:
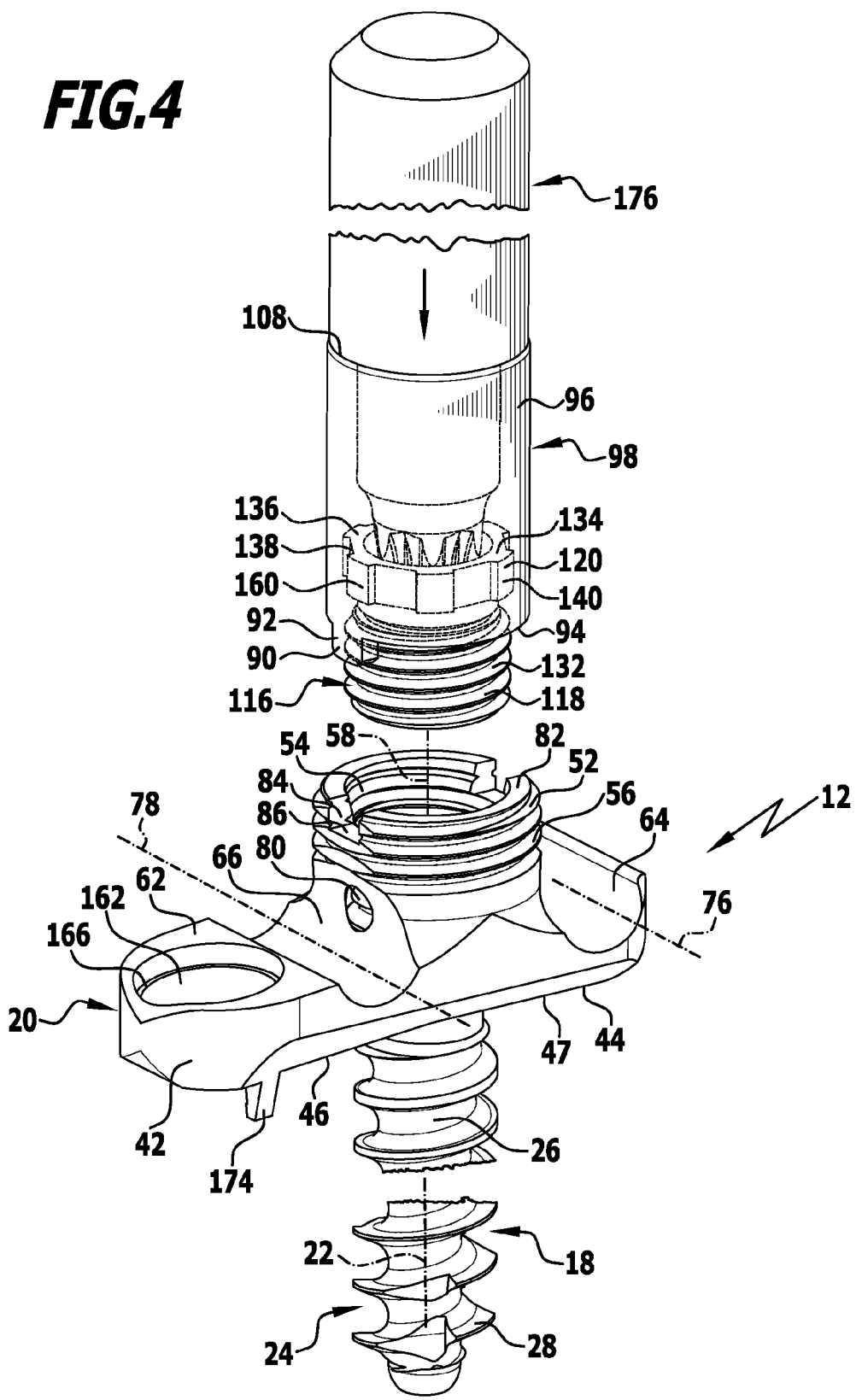
FIG. 4 shows a perspective view of the bone anchoring device from FIG. 3 during preassembly of a centering element by means of a fixing element.

Optionally, an anchoring element 174, for example, in the form of a retaining spike, as represented diagrammatically, for example, in FIGS. 3 and 4, may protrude from the underside 44 of the main body 42. The anchoring element 174 forms an additional lock against rotation when it penetrates a vertebra 14.

The bone anchoring device 12 is preassembled as unit and comprises the anchoring part 18 and the bearing part 20 and optionally the centering element 98 and the fixing element 116. As shown in FIG. 3, the screw shaft 26 is first guided with its distal end from the proximal end through the sleeve section 52 until the screw head 30 bears on the seat 48.

Furthermore, the fixing element 116 is inserted with its distal fixing element section 118 from the proximal end into the end 108 of the centering element 98. In relation to the longitudinal axis 58, the fixing element 116 is so aligned relative to the centering element 98 that the internal toothing 110 and the external toothing 140 can engage and the fixing element 116 can be advanced in the distal direction until the first and second coupling members 152 and 154 bear on each other. Using a screwing-in tool 176 having a distal tool end 178 corresponding constructionally to the tool element receptacle 128, the external thread section 132 can be screwed to the internal thread 54, namely precisely until the end faces 82 and 94 bear on each other. Here care must be taken to ensure that the predetermined break-off area 122 is not destroyed. The screwing-in tool 176 is therefore preferably equipped with a torque delimitation so that only a torque that is smaller than a fracture torque of the predetermined break-off area 122 is applied.

After removal of the screwing-in tool 176, the bone anchoring device 12 is preassembled with centering element 98 for implantation in a vertebra 14.

Possibilities for implantation of the spinal column fixation system 10 using suitable instruments provided therefor will be explained in detail hereinbelow step by step with reference to FIGS. 1 to 20.

If a cannulated bone screw 24, as described above, is used as anchoring part 18, in an optional first step, after opening an access to the human body, a K-wire insertion instrument generally denoted by reference numeral 180 can be used to place the K-wire 36 in the vertebra 14. The K-wire insertion instrument 180 comprises an elongate guide sleeve 182 with a cutting distal end 184. A proximal end of the K-wire insertion instrument 180 forms a hollow cylinder 186 which is mounted in a rotationally fixed manner coaxially with a longitudinal axis 188 of the guide sleeve 182, with a holding grip 190 protruding therefrom in a direction transverse to the longitudinal axis 188. The hollow cylinder 186 is open so as to face in the proximal direction and defines a ring surface 192 facing in the proximal direction, which serves as striking surface for driving the distal end 184 into the vertebra 14.

The K-wire 36 is of two-part construction and comprises a distal section 194 and a proximal section 196, which are connected to each other by a coupling device 198. In particular, the coupling device 198 may be in the form of a screw connection for screwing the distal section 194 and the proximal section 196 to each other. A piston body 202 comprising a distal piston section 204 and a proximal piston section 206 is arranged at a proximal end 200 of the proximal section 196. The distal piston section 204 is of such dimensions that it can be inserted in a positively locking manner into the hollow cylinder 186 from the proximal end, namely such that the K-wire 36 can be guided with its distal, sharpened end 208 through the guide sleeve 182 and advanced beyond the end 184. The proximal piston section 206 is larger in its outer diameter than the hollow cylinder 186 and forms a stop for the hollow cylinder 186, thereby delimiting movement of the K-wire 36 in the distal direction. The end 208 projects to a maximum extent beyond the end 184 when the proximal piston section 206 bears on the ring surface 192.

A radially projecting ring flange 210 facing away from the longitudinal axis 188 is arranged at a distance from the end 184 for delimiting a drive-in depth of the guide sleeve 182 into the vertebra.

Figure 2:
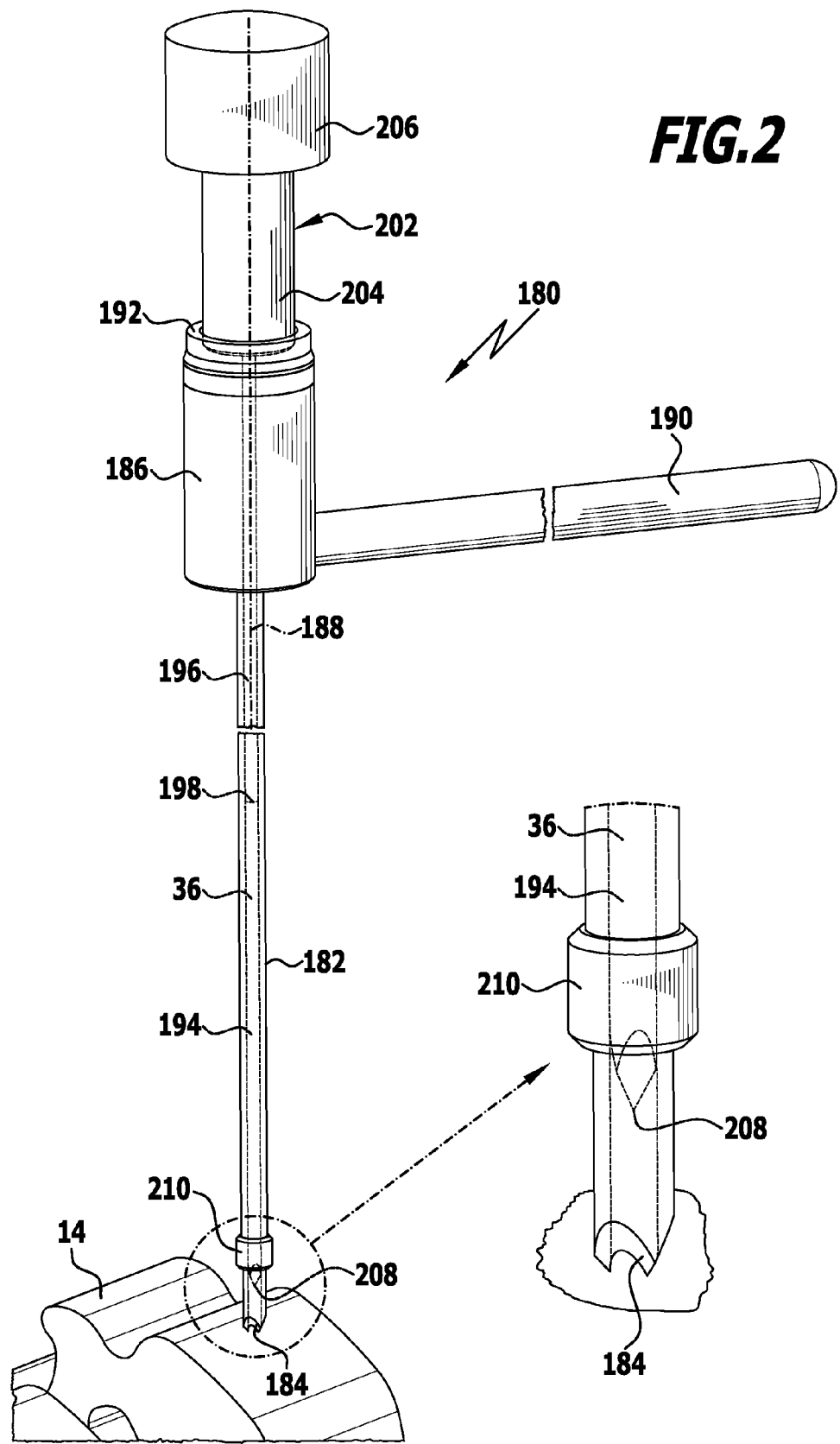
FIG. 2 shows a partly broken-open side view during application of the K-wire to a vertebra using the instrument shown in FIG. 1.

As represented diagrammatically in FIG. 2, the K-wire insertion instrument 180 is preferably first driven into the vertebra 14 without the K-wire 36, and the K-wire 36 is then inserted in the described manner through the guide sleeve 182 and driven into the vertebra 14. When the K-wire 36 is placed in the desired manner in the vertebra 14, the proximal section 196 is separated from the distal section 194, for example, screwed off. The K-wire insertion instrument 180 is then also removed from the vertebra 14. Only the distal section 194 of the K-wire 36 then remains in the vertebra 14.

Next, the bone anchoring device 12 preassembled as described above is prepared with centering sleeve 96 for the implantation. To enable it to be inserted into the patient's body, it is first connected to a holding instrument generally denoted by reference numeral 212. The holding instrument 212 comprises a guide sleeve 214 which is connectable to the centering sleeve 96 coaxially with the longitudinal axis 58. The outer diameter of the guide sleeve 214 corresponds to the outer diameter of the centering element 98. The guide sleeve 214 can be axially connected in a rotationally fixed manner to the centering element 98 by a connecting device generally denoted by reference numeral 216. A plurality of slots 220 extending from a distal end 218 of the guide sleeve 214 parallel to the longitudinal axis 58 and distributed over the circumference of the guide sleeve 214 define resilient arms 222 between them. A radially projecting ring flange 224 facing away from the longitudinal axis 58 adjacent to the end 218 is interrupted by the slots 220. The resilient arms 222 with the ring flange 224 formed in sections form locking elements of the connecting device 216 which is configured as a locking connection. At a distance from the ring flange 224, proximally thereof, an external toothing 226 is formed on the guide sleeve 214, namely with a plurality of projections 228 extending parallel to the longitudinal axis 58 and distributed over the circumference. The external toothing 226 corresponds constructionally to the internal toothing 110. The projections 228 are set back somewhat in relation to an outer surface 230 of the guide sleeve 214, so that each projection 228 has associated with it a stop surface 232 facing in the distal direction and adjoining it proximally.

The guide sleeve 214 is connected to the centering element 98 as follows. The end 218 is inserted from the proximal end into the centering sleeve 96, which is already secured with the fixing element 116 to the bearing part 20. The remaining sections of the ring flange 224 on the resilient arms 222 thereby slide up the internal toothing 110 and are pretensioned somewhat in the direction towards the longitudinal axis 58. The guide sleeve 214 is rotated about the longitudinal axis 58 so as to enable the external toothing 226 to engage with the internal toothing 110. It is thereby possible to advance the guide sleeve 214 in the distal direction until the stop surfaces 232 strike the proximal end 108 of the centering sleeve 96. The resilient arms 222 are of such length and the ring flange 224 so positioned that when the stop surfaces 232 bear against the end 108, the resilient arms 222 can spring out radially again away from the longitudinal axis 58 distally of the internal toothing. In this way, the guide sleeve 214 and the centering sleeve 96 are connected to each other in an axially locked and rotationally fixed manner.

A proximal end of the guide sleeve 214 is provided with a hexagon head 234 which forms a coupling member for connecting the guide sleeve 214 to a handle 236. The handle 236 preferably projects in a direction perpendicular to the longitudinal axis 58 from the guide sleeve 214. It is provided with a corresponding coupling body 238 which enables a connection with force locking and positive locking to the hexagon head 234 of the guide sleeve 214. The handle 236 may be either releasably connectable or permanently connected to the guide sleeve 214.

Figure 8:
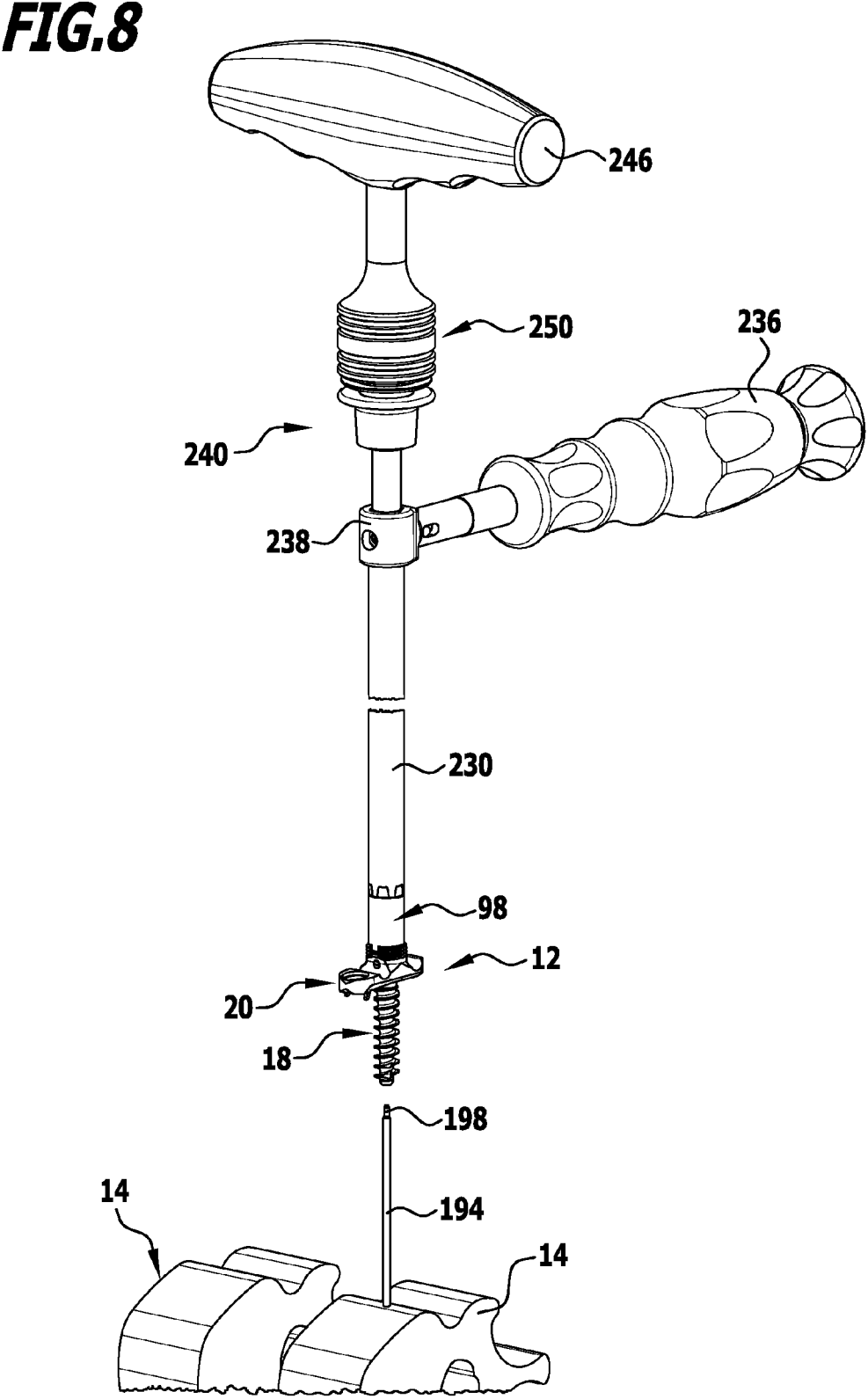
FIG. 8 shows a perspective general view of the assembly from FIG. 7 with additional screwing-in tool for the anchoring part of the bone anchoring device while being pushed onto the K-wire inserted in the vertebra.

After connection of the holding instrument 212 to the bone anchoring device 12, a surgeon can comfortably hold the entire unit by the handle 236, insert the bone screw 24 into the patient's body and thread it onto the K-wire 36, as represented diagrammatically in FIG. 8. The bone anchoring device 12 still assumes the assembly position, which means that the anchoring part 18 and the bearing part 20 are connected to each other as a ball-and-socket joint.

Optionally, for better guidance of the bone anchoring device 12, the surgeon may now insert into the guide sleeve 214 from the proximal end a screwing-in tool 240 for screwing the bone screw 24 into the vertebra. The screwing-in tool 240 has a distal tool end 242, which corresponds constructionally to the tool receptacle 40 and is insertable in it from the proximal end. This is represented diagrammatically in FIG. 9.

Figure 9:
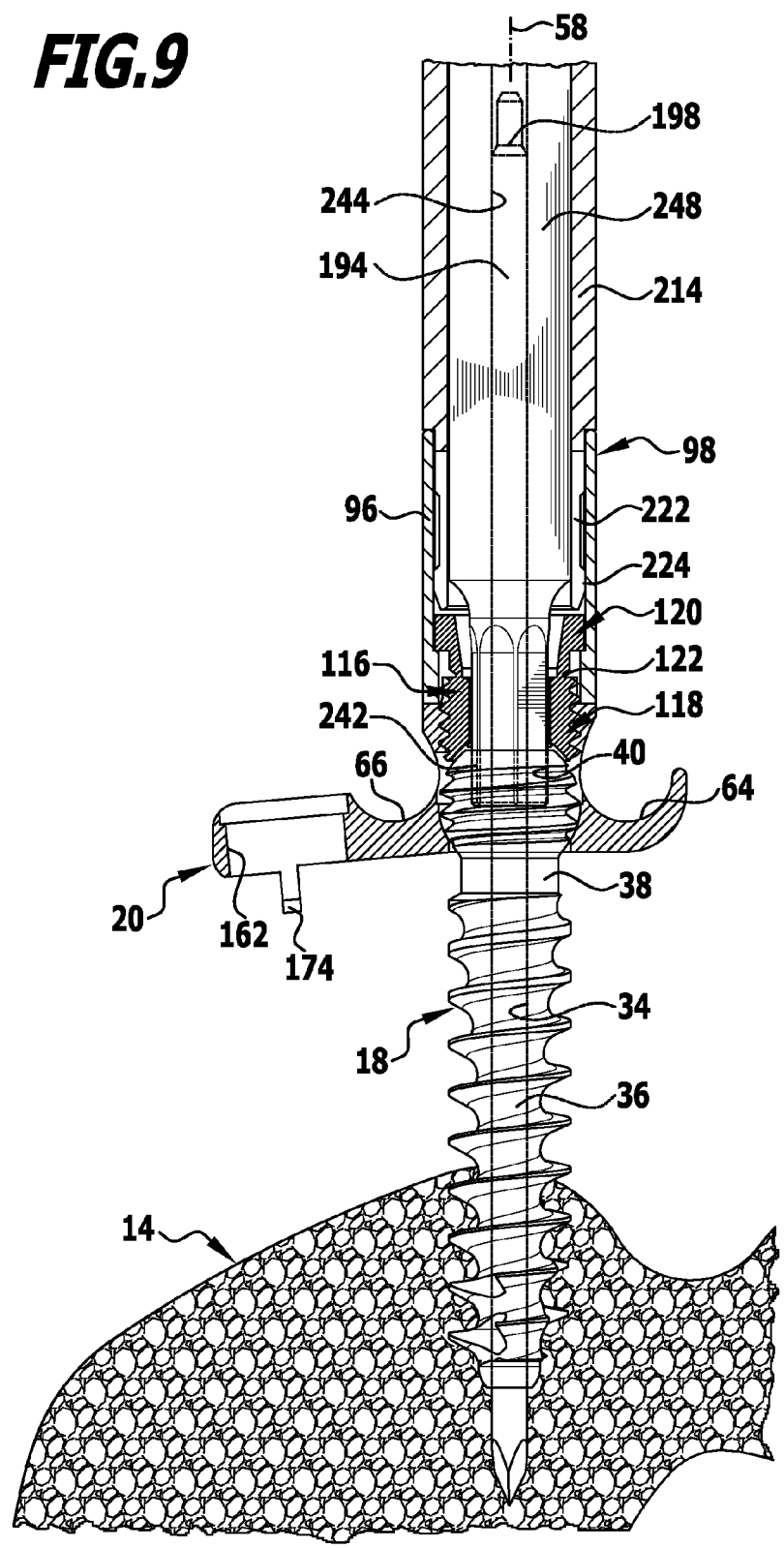
FIG. 9 shows a longitudinal sectional view of a distal end area of the overall assembly shown in FIG. 8 while screwing in the anchoring part.
Figure 10:
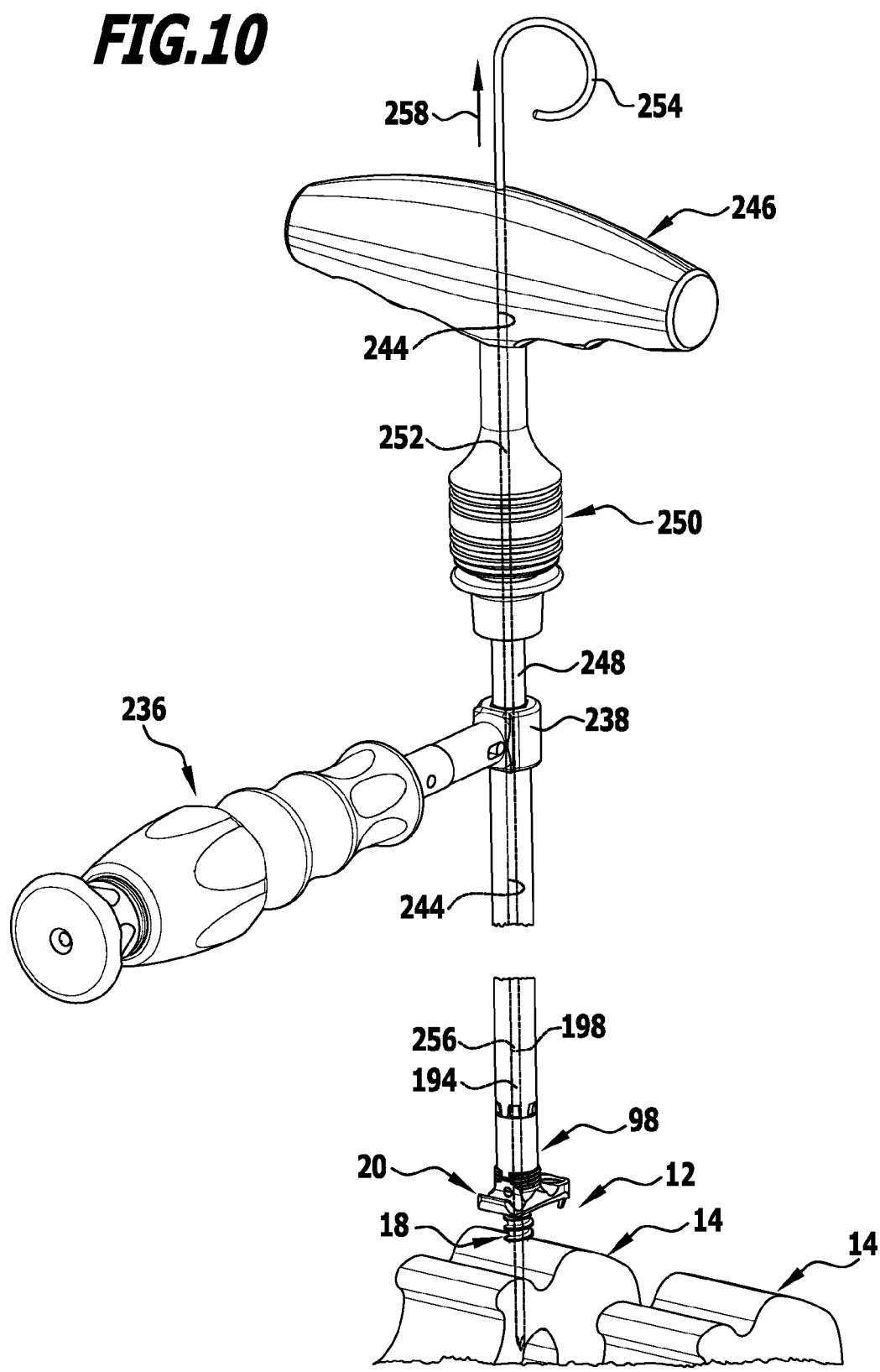
FIG. 10 shows a view similar to FIG. 8 after screwing-in of the anchoring part into the vertebra while withdrawing the K-wire from the vertebra using a K-wire removal instrument.
Figure 11:
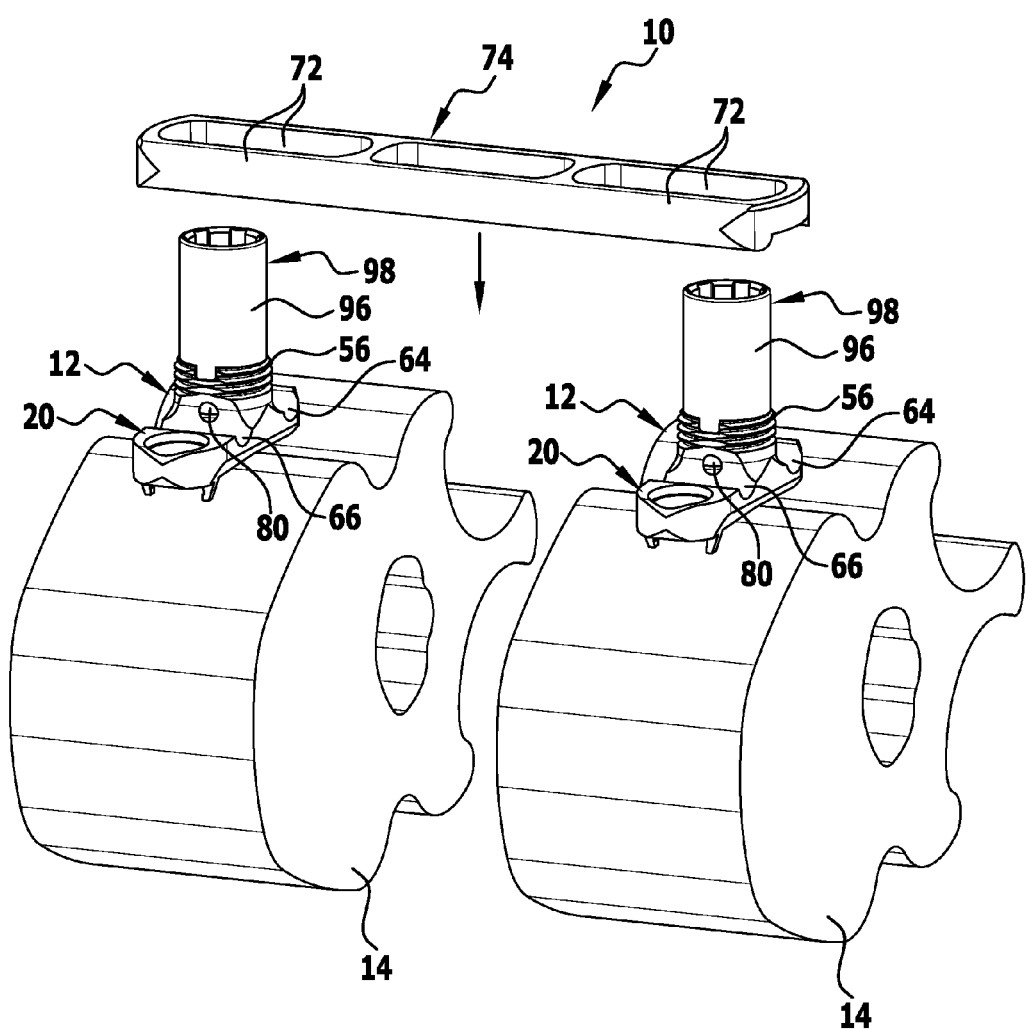
FIG. 11 shows a perspective general view of two diagrammatically represented vertebrae while connecting these using a connection plate by placement of thereof onto two bone anchoring devices anchored in the vertebra.

As represented diagrammatically in FIGS. 9 and 10, the screwing-in tool 240 is provided over its entire length with a wire channel 244 which extends coaxially with the longitudinal axis 58. The tool end 242 forms a distal end of a shaft 248 of the screwing-in tool 240 at the proximal end of which a torque delimiting unit generally designated by reference numeral 250 is arranged. A T-shaped grip 246 is formed proximally of the torque delimiting unit.

As represented diagrammatically in FIGS. 8 and 9, a surgeon can now hold the handle 236 with one hand and with the screwing-in tool 240 by holding the grip 246 move the bone anchoring device 12 up to and guide it over the K-wire 36 until a distal end of the bone screw 24 comes into contact with the vertebra 14. To drive the bone screw 24 into the vertebra 14, the surgeon turns the grip 246 in the clockwise direction until the bone screw 24 is securely placed in the vertebra 14.

Once the bone screw 24 itself is held in the vertebra 14, the K-wire 36, i.e. its distal section 194 can be removed again. For this purpose, a removal wire 252 with a bent proximal end 254 is introduced from the proximal end through the wire channel 244. A distal end 256 of the removal wire 252 is configured for connection, for example, by screwing, to the proximal end of the distal section 194. After connection of the distal section 194 to the removal wire 252, this newly created wire unit can be pulled in the proximal direction out of the vertebra 14 by the surgeon pulling the end 254 in the direction of arrow 258.

Furthermore, the screwing-in tool 240 and the holding instrument 212 can be removed from the bone anchoring device 12.

In an analogous manner, a further bone screwing device 12 is introduced into the adjacent vertebra 14. The plate-shaped connection element 74 can now be pushed over the two centering elements 98 of the two bone anchoring devices 12 anchored in the adjacent vertebrae 14, namely such that a respective section 72 of the connection element 74 engages each connection element receptacle 64 and 66, respectively, of the two bearing parts 20.

To enable fixing of the vertebrae 14 at a distance specified by the surgeon, the connection element 74 must be fixedly connected to the bone anchoring device 12. A clamping device denoted generally by reference numeral 260 serves this purpose. This comprises a nut 264 with an internal thread 262. The internal thread 262 corresponds constructionally to the external thread 56 of the sleeve section 52. When the nut 264 is screwed onto the sleeve section 52, the sections 72 can be pressed by the nut 264 into the connection element receptacles 64 and 66 and held clamped therein. The nut 264 thereby reduces in size at least partially insertion openings 266 and 268 opened transversely to the longitudinal axes 76 and 78 defined by the connection element receptacles 64 and 66 in a clamped position. This is diagrammatically clearly apparent from FIG. 19.

A screwing tool generally denoted by reference numeral 270 comprising a sleeve 272 extending coaxially with the longitudinal axis 58 serves for insertion of the nut 264. An inner diameter of the sleeve 272 is of such dimensions that the guide sleeve 214 of the holding instrument 212 can be guided through the sleeve 272. A proximal end of the screwing tool 270 is in the form of a T-grip 274 and comprises a hexagonal head 276 protruding in the proximal direction, which is formed coaxially with the longitudinal axis 58 and is fixedly connected to the sleeve 272. A distal end 280 of the sleeve 272 is in the form of a nut receptacle 278 into which the nut 264 can be inserted. Preferably, the nut receptacle 278 is so constructed that the nut 264 is lockable to the nut receptacle 278 in order to prevent the nut 264 from falling out of the nut receptacle 278 when inserted into the patient's body.

Figure 12:
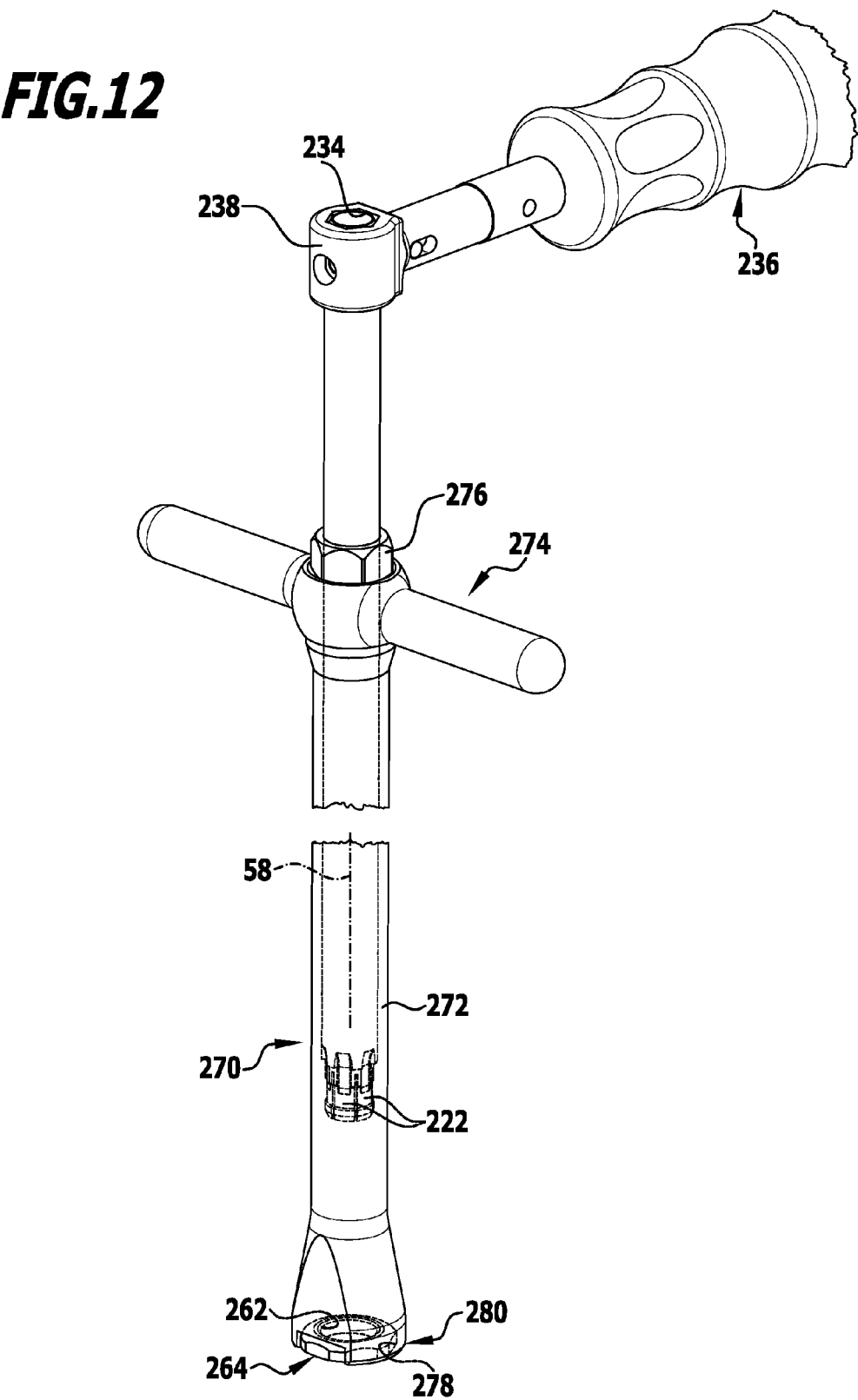
FIG. 12 shows a perspective, partly broken-open general view of the holding and insertion instrument during insertion into a screw-in sleeve with a fastening nut held therein.
Figure 13:
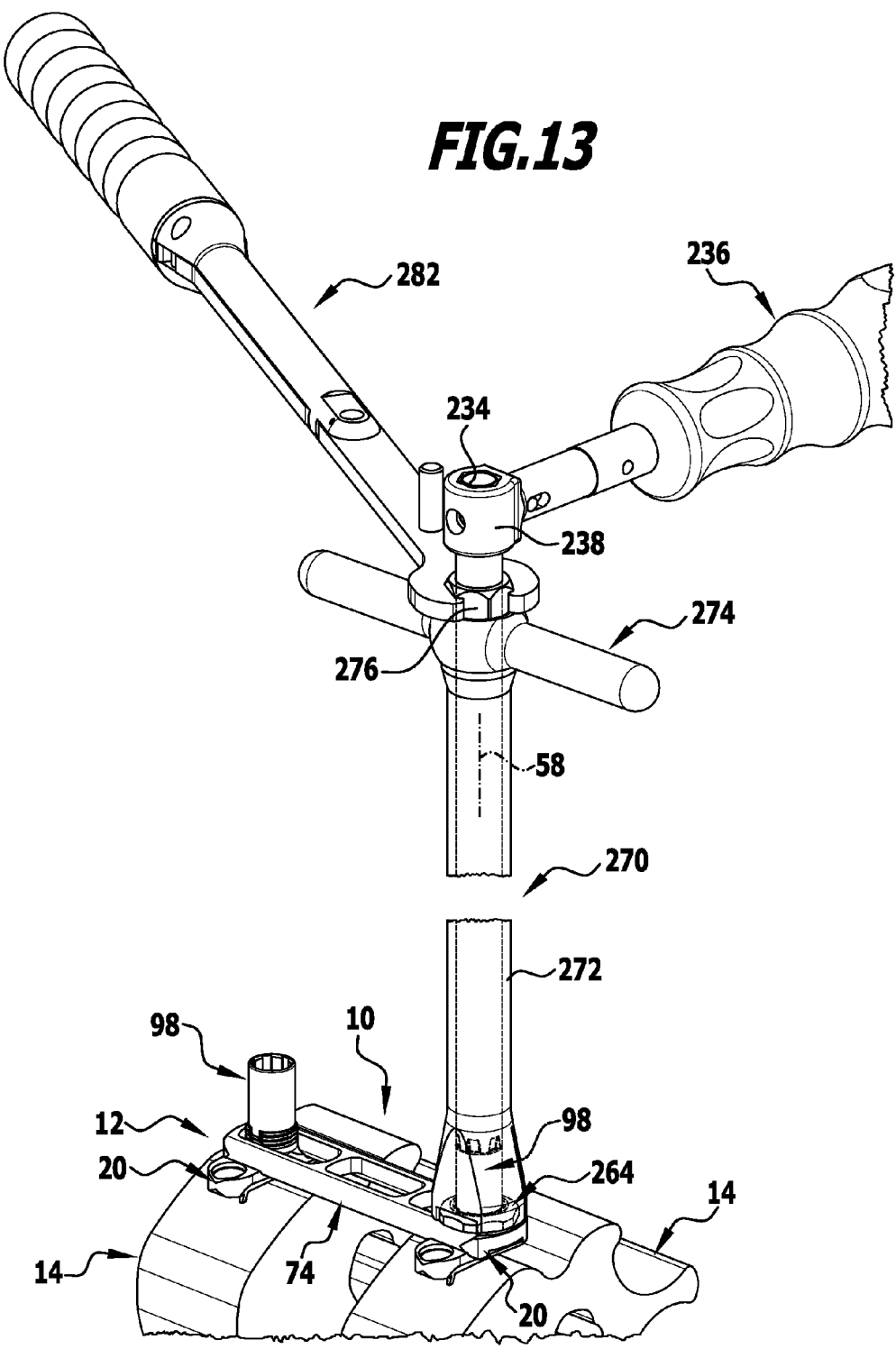
FIG. 13 shows a perspective, partly broken-open general view of the assembly from FIG. 12 while tightening the fastening nut to a bearing part of one of the two bone anchoring devices with a torque wrench.

As represented diagrammatically in FIG. 12, the nut 264 inserted in the nut receptacle 278 can now be guided with the screwing tool 270 over the centering sleeve 96 and by turning the T-grip 274 in the clockwise direction screwed to the sleeve section. Once the nut 264 is brought by the screwing tool 270 up to the connection element 74, the holding instrument 212 is again coupled in the above-described manner by the connecting device 216 to the centering element 98. The handle 236 now projects proximally from the sleeve 272. The holding instrument 212 serves to withstand the tightening torque introduced by a torque wrench 282 into the hexagonal head 276 for tightening the nut 264. Once the torque wrench 282 disengages when the preset tightening torque is exceeded the torque wrench 282 is removed. The holding instrument 212 and the screwing tool 270 are then released from the bone anchoring device 12 and removed.

In analogy with the described procedure, a further nut 264 is screwed to the other bone anchoring device 12. The Figures do not show that, if necessary, distraction tools may be used to distract the adjacent vertebrae 14 in the desired manner.

Figure 14:
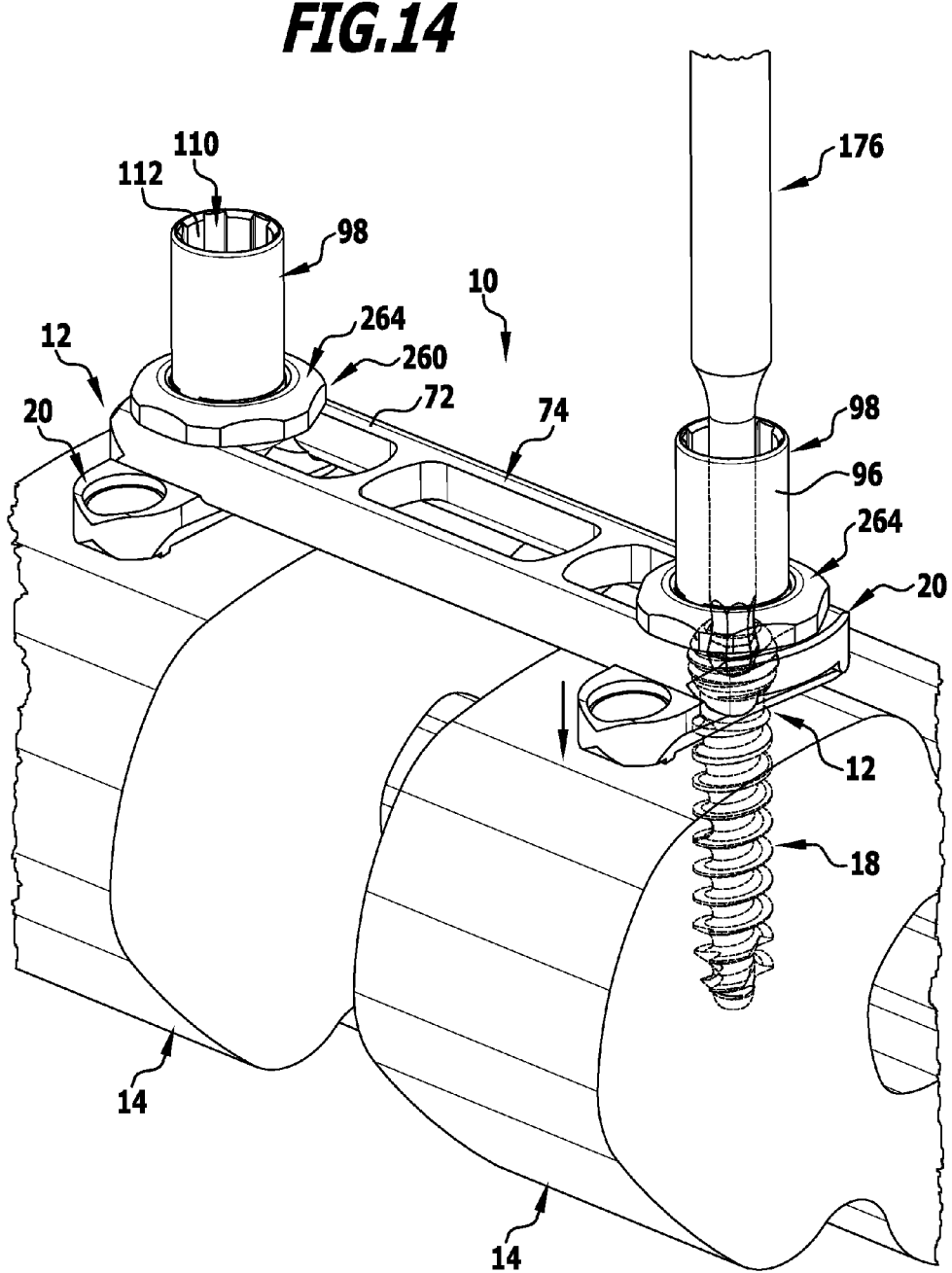
FIG. 14 shows a perspective general view similar to FIG. 11 of the spinal column fixation system, wherein the connection plate is tightened by two fastening nuts, during the final tightening of the anchoring part of one of the two bone anchoring devices.
Figure 16:
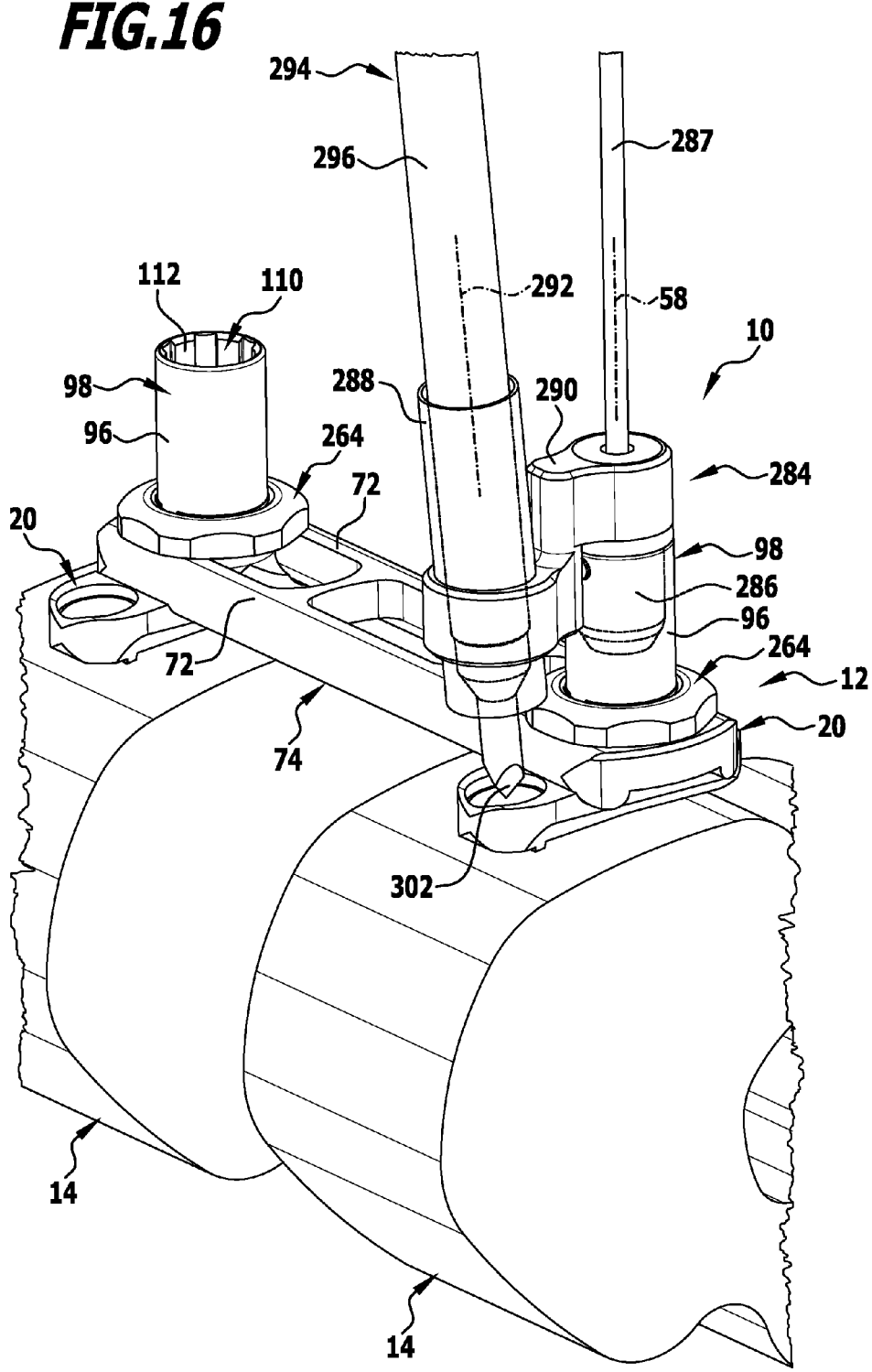
FIG. 16 shows a partly broken-open, enlarged view of the overall assembly from FIG. 15.

As represented diagrammatically in FIG. 14, the two bone anchoring devices 12 are now fixedly connected to each other by the connection element 74. However, the bearing parts 20 and the anchoring parts 18 can still be pivoted relative to each other.

Since the bearing parts 20 were preferably screwed into the vertebrae 14 by the bone screw 24 only to such an extent that the anchoring elements 174 do not yet engage the vertebrae 14, the bone screw 24 must be screwed even further into the vertebrae 14 for final securing of the bearing parts on the vertebrae 14. For this purpose, the tool end 178 of the screwing-in tool 176 is again brought into engagement with the tool receptacle 40 on the screw head 30, and the bone screw 24 is screwed into the vertebra 14 until the underside 44 bears essentially with surface-to-surface contact on an outer side of the vertebra 14. The spike-shaped anchoring element 174 then engages the vertebra 14 and prevents rotation of the bearing part 20 about the longitudinal axis 58.

If, as described above, the bearing parts 20 that are used have additional fastening element receptacles 162, these may be used to secure the bearing parts 20 with additional fastening elements 164 against rotation about the longitudinal axis 58. To enable insertion of the fastening elements 164 in a defined manner, an aligning instrument 284 may be optionally used by a surgeon. It comprises a coupling pin 286 which is introducible from the proximal end in a positively locking manner into the centering sleeve 96. The coupling pin 286 is brought up to the bone anchoring device by way of a guide wire 287 inserted in the longitudinal bore 34 and is coupled to an aligning sleeve 288 by a holding body 290. A longitudinal axis 292 of the aligning sleeve 288 is automatically positioned so as to coincide with the longitudinal axis 172. By means of a marking instrument 294 comprising an elongate shaft 296, having arranged at its proximal end a grip 298 with a striking surface extending transversely to the longitudinal axis 292, and a distal end in the form of a pointed spike 302, the aligning sleeve 288 is positioned on the vertebra 14. The shaft 296 is adapted with its outer diameter to the inner diameter of the aligning sleeve 288. The spike 302, may, for example, be driven into the vertebra 14 by striking the striking surface 300 with a hammer which is not shown.

After removal of the marking instrument 294, the fastening element 164, for example, in a form of a bone screw, can be introduced through the aligning sleeve 288 and screwed with a suitable screwing-in tool 304 into the vertebra 14. By marking the vertebra 14 with the spike 302 it is ensured that the fastening element 164 can be introduced in the desired manner into the vertebra 14.

Figure 17:
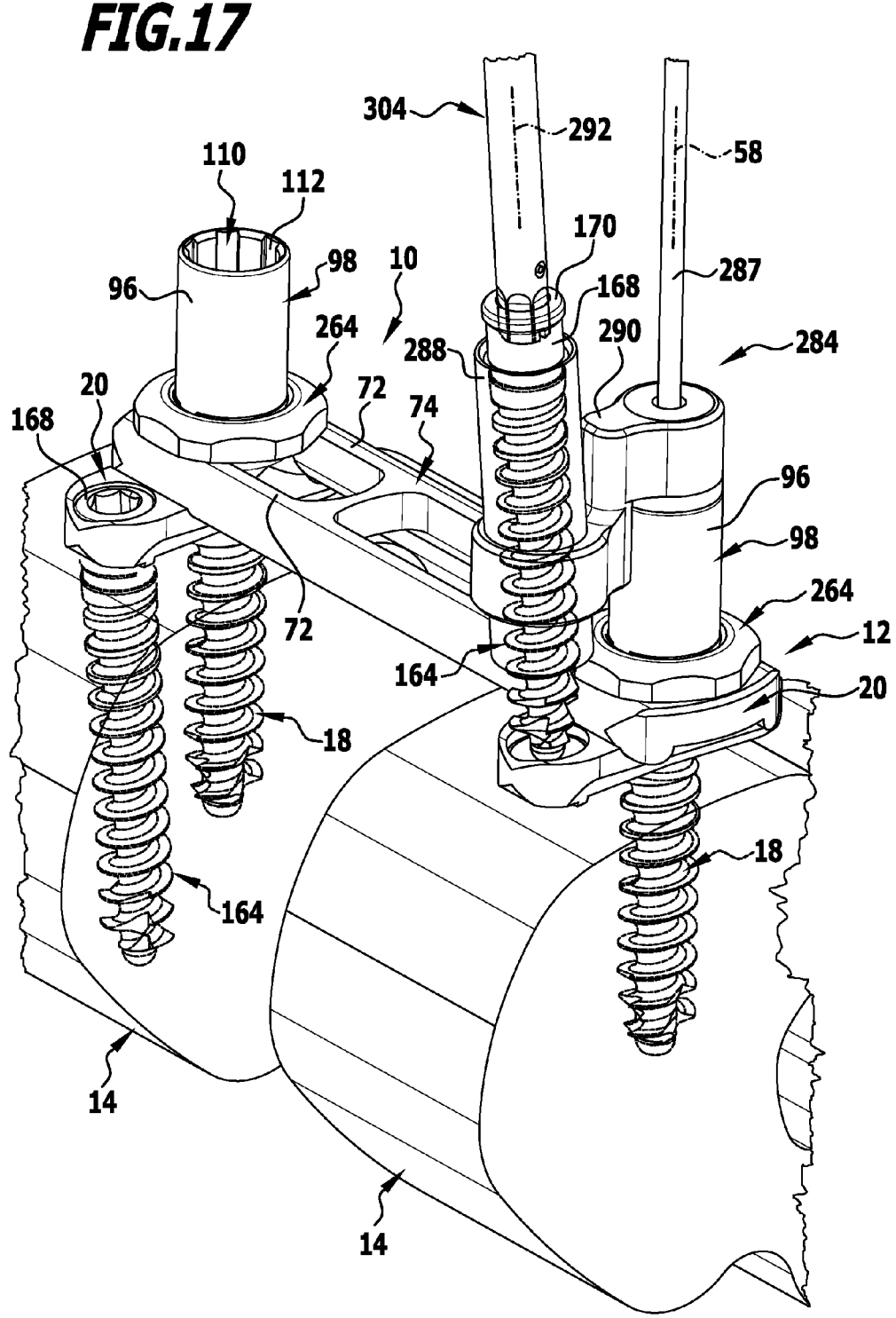
FIG. 17 shows a view in analogy with FIG. 16 while screwing in an additional fastening screw using the targeting device.
Figure 18:
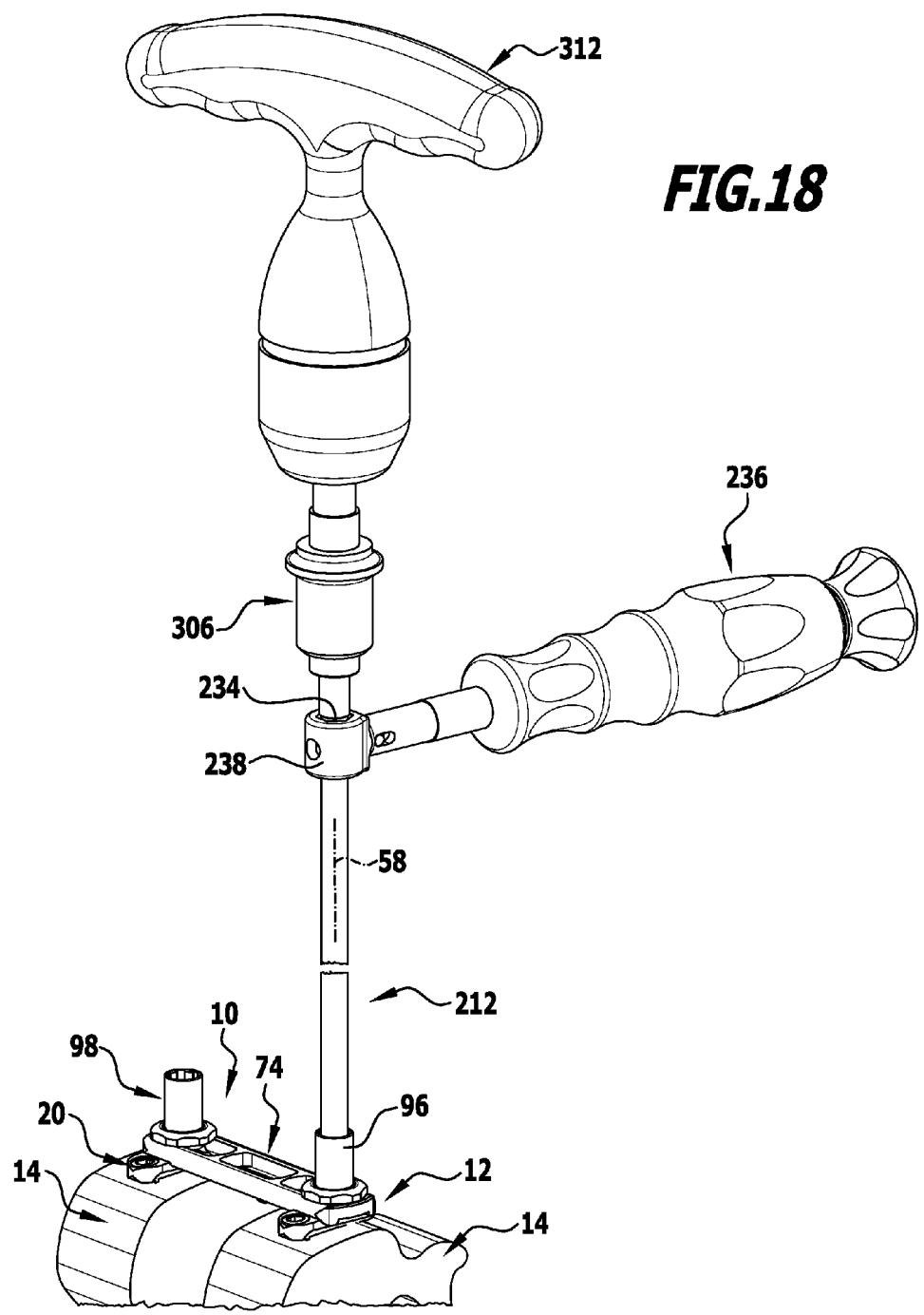
FIG. 18 shows a view similar to FIG. 15 but while tightening the fixing element using a torque wrench.
Figure 19:
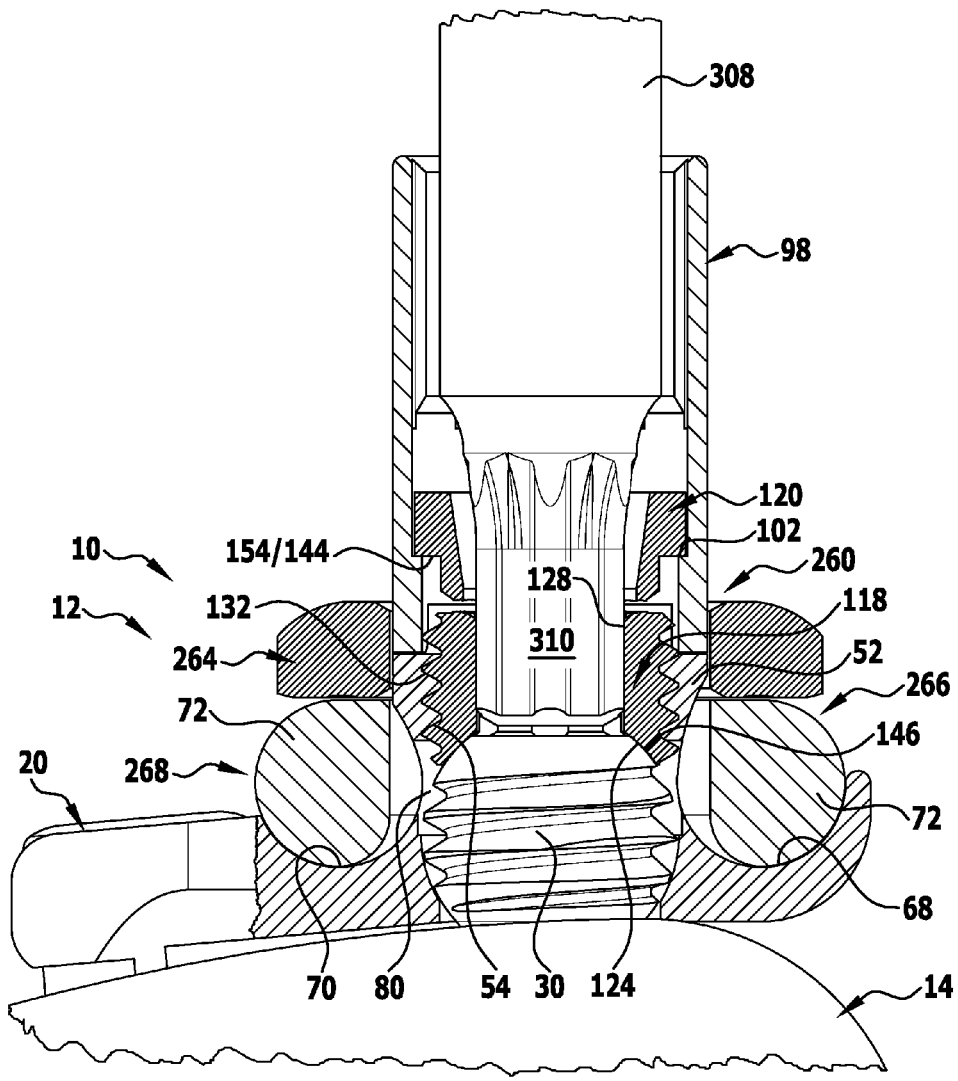
FIG. 19 shows an enlarged, partly sectional view of the assembly shown in FIG. 18 while tightening the fixing element after severing of a predetermined break-off area thereof.

As represented diagrammatically in FIGS. 17 and 18, the spinal column fixation system 10 is now fixed to the vertebrae 14. However, the bearing parts 20 and the anchoring parts 18 are not yet tensioned against each other as the fixing surface 124 and the fixing surface area 146 are still spaced from each other. Therefore, in a last step, the fixing element 116 has to be tensioned in the distal direction against the screw head 30, namely such that the fixing surface 124 presses against the fixing surface area 146. For this purpose, the holding instrument 212 is again coupled to the centering element 98 in the manner described above.

A shaft 308 of a further torque wrench 306 is introduced through the guide sleeve 214. At its distal end, the torque wrench 306 is in the form of a tool end 310 which is engageable with the tool element receptacle 128. In particular, the torque wrench 306 may be the screwing-in tool 176. It should be noted that the tool end 310 is exclusively in engagement with the tool element receptacle 128, and not with the proximal fixing element section 120. This means that only torques can be transmitted to the distal fixing element section 118 by the torque wrench 306. A surgeon preferably holds the hand grip 236 with one hand and turns a T-shaped grip 312 of the torque wrench 306 in the clockwise direction with his other hand. As described above, the stop surfaces 102 and 144 bear against each other, so that the predetermined break-off area 122 is increasingly subjected to both tension and torsion by the applying of a torque with the torque wrench 306. When a fracture torque of the predetermined break-off area 122 is exceeded, the predetermined break-off area 122 is destroyed by the tensile and torsional forces that are introduced and the distal fixing element section 118 is irreversibly separated from the proximal fixing element section 120. With the torque wrench 306 the distal fixing element section 118 can now be moved further in the distal direction until the torque wrench 306 disengages when a preset torque is exceeded. The preset torque on the torque wrench 306 corresponds to the desired tightening torque with which the distal fixing element section 118 is to be tensioned against the screw head 30. The fixing element 116 or its distal fixing element section 118 therefore forms a clamping element for holding the screw head 30 of the anchoring part 18 in a clamped manner in the seat 48 of the bearing part 20.

The torque wrench 306 can now be pulled in the proximal direction out of the guide sleeve 214. The holding instrument 212 is still coupled to the centering element 98. Since the distal fixing element section 118 and the proximal fixing element section 120 are separate from each other, there is now no longer any fixed connection between the centering element 98 and the bearing part 20. The centering element 98 can therefore be removed in the proximal direction from the bearing part 20 by the holding instrument 212 coupled to it. The proximal fixing element section 120 is, however, held in the manner described above on the centering sleeve 96 and is unable to fall out of it. It is removed from the surgical site simultaneously with removal of the centering sleeve 96.

Figure 20:
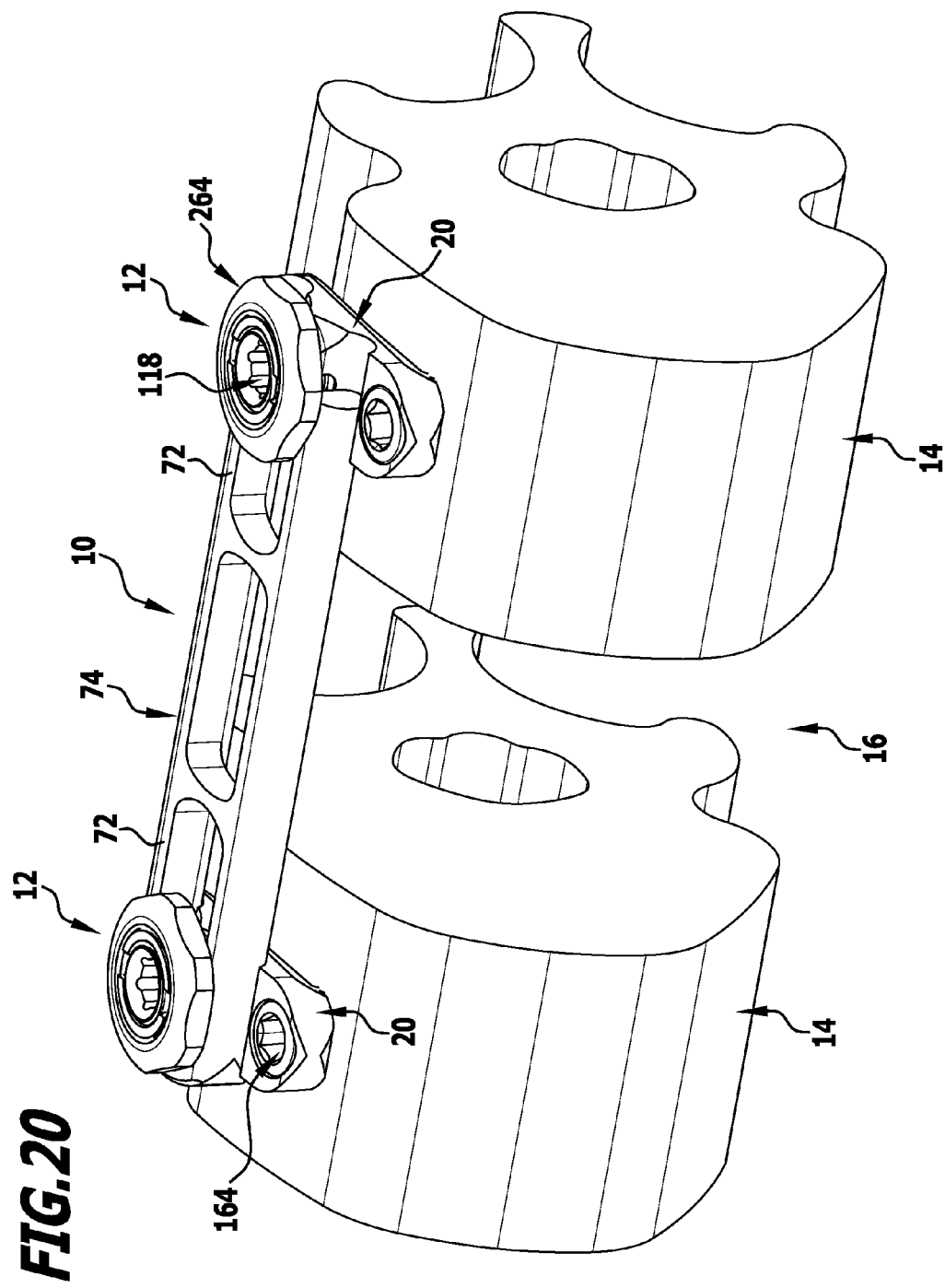
FIG. 20 shows a perspective general view of the spinal column fixation system fixed to two vertebrae.

As shown in FIG. 20, the two adjacent vertebrae 14 are now permanently fixedly connected to each other in the desired manner at a specified distance from each other.

The centering element 98 preassembled on the bearing part 20 therefore only temporarily forms part of the anchoring device 12. At the end, the fixing element 116 only remains with its distal fixing element section 118 in the patient's body. The proximal fixing element section 120 therefore forms together with the centering sleeve 96 part of the instrumentation described and is removed in the described manner before the patient's body is closed.

The invention claimed is:

1. A surgical bone anchoring device for a spinal column fixation system, the surgical bone anchoring device comprising:
    an anchoring part adapted for anchoring in or on a bone;
    a bearing part adapted for mounting of at least one connection element thereon, said connection element being adapted for fixing to at least two bone anchoring devices of the spinal column fixation system;
    a fixing element provided with an external thread section, a proximal fixing element section and a distal fixing element section; and
    a centering element which is held by the fixing element on the bearing part,
    the centering element comprising a first stop surface facing in a proximal direction, and the fixing element comprising a second stop surface on the proximal fixing element section facing in a distal direction,
    wherein the first stop surface and second stop surface engage and bear against one another in a coupling position which limits movement of the proximal fixing element section in a distal direction relative to the centering element,
    wherein said anchoring part and said bearing part are mounted on each other, movable relative to each other in an assembly position and fixable relative to each other by the fixing element in an implantation position, said fixing element being of integral construction and having a predetermined break-off area formed between the proximal fixing element section and the distal fixing element section, and the distal fixing element section having provided therein a tool element receptacle for engagement by force locking and/or positive locking with a tool for moving the bone anchoring device from the assembly position to the implantation position,
    wherein the bearing part is formed from one piece and comprises an internal thread section which corresponds to the external thread section of the fixing element.

2. The surgical bone anchoring device in accordance with claim 1, wherein the centering element is in the form of a centering sleeve.

3. The surgical bone anchoring device in accordance with claim 1, wherein a positioning device is provided for positioning the centering element and the bearing part relative to each other in the assembly position.

4. The surgical bone anchoring device in accordance with claim 3, wherein the positioning device comprises first and second positioning members which are arranged or formed, on the one hand, on the centering element and, on the other hand, on the bearing part, and wherein the first and second positioning members engage one another by force locking and/or positive locking in the assembly position.

5. The surgical bone anchoring device in accordance with claim 4, wherein the first and second positioning members face in a direction parallel to a longitudinal axis of the centering element.

6. The surgical bone anchoring device in accordance with claim 3, wherein the positioning device and the first and second stop surfaces secure the centering element in the assembly position and in the coupling position on the bearing part so that the centering element is unable to rotate about a longitudinal axis defined by the centering element.

7. The surgical bone anchoring device in accordance with claim 1, wherein the fixing element holds the centering element immovably on the bearing part in the assembly position.

8. The surgical bone anchoring device in accordance with claim 1, wherein the fixing element holds the centering element by force locking and/or positive locking on the bearing part in the assembly position.

9. The surgical bone anchoring device in accordance with claim 1, wherein the fixing element holds the centering element clamped on the bearing part in the assembly position.

10. The surgical bone anchoring device in accordance with claim 1, wherein the first stop surface and the second stop surface engage and bear against one another in said coupling position when the bone anchoring device assumes the assembly position.

11. The surgical bone anchoring device in accordance with claim 1, wherein the fixing element has a fixing element surface which, in the implantation position, bears on a fixing surface area of the anchoring part, and wherein the fixing surface is spaced from the fixing surface area when the first and second stop surfaces assume the coupling position and so long as the distal and proximal fixing element sections are connected to each other via the predetermined break-off area.

12. The surgical bone anchoring device in accordance with claim 1, wherein the bearing part and the anchoring part are movable relative to each other when the predetermined break-off area is undamaged.

13. The surgical bone anchoring device in accordance with claim 1, wherein the distal and proximal fixing element sections are irreversibly separable from each other by destroying the predetermined break-off area.

14. The surgical bone anchoring device in accordance with claim 1, wherein the predetermined break-off area is formed by a weakening of the fixing element between the distal and proximal fixing element sections.

15. The surgical bone anchoring device in accordance with claim 1, wherein the predetermined break-off area borders proximally on the external thread section of the fixing element.

16. The surgical bone anchoring device in accordance with claim 1, wherein the proximal fixing element section has a larger outer diameter than the distal fixing element section.

17. The surgical bone anchoring device in accordance with claim 1, wherein a clamping device is provided for holding a connection element of the spinal column fixation system in a clamped manner on the bearing part.

18. The surgical bone anchoring device in accordance with claim 1, wherein a securing device is provided for securing the proximal fixing element section on the centering element after separation of the distal and proximal fixing element sections from each other.

19. The surgical bone anchoring device in accordance with claim 1, wherein the securing device comprises an internal toothing on the centering element proximally of the first stop surface provided on the centering element, and a corresponding external toothing of the proximal fixing element section.

20. The surgical bone anchoring device in accordance with claim 1, wherein the fixing element is in the form of a clamping element for holding in a clamped manner a head section of the anchoring part in a seat of the bearing part for the head section.

21. A spinal column fixation system comprising at least one surgical bone anchoring device, said at least one surgical bone anchoring device comprising:
an anchoring part adapted for anchoring in or on a bone;
a bearing part adapted for mounting of at least one connection element on the bearing part, said connection element being adapted for fixing to at least two bone anchoring devices of the spinal column fixation system;
a fixing element provided with an external thread section, a proximal fixing element section and a distal fixing element section; and;
a centering element which is held by the fixing element on the bearing part,
the centering element comprising a first stop surface facing in a proximal direction, and the fixing element comprising a second stop surface on the proximal fixing element section facing in a distal direction,
wherein the first stop surface and second stop surface engage and bear against one another in a coupling position which limits movement of the proximal fixing element section in a distal direction relative to the centering element,
wherein said anchoring part and said bearing part are mounted on each other, movable relative to each other in an assembly position and fixable relative to each other by the fixing element in an implantation position, said fixing element being of integral construction and having a predetermined break-off area formed between the proximal fixing element section and the distal fixing element section, and the distal fixing element section having provided therein a tool element receptacle for engagement by force locking and/or positive locking with a tool for moving the bone anchoring device from the assembly position to the implantation position,
wherein the bearing part is formed from one piece and comprises an internal thread section which corresponds to the external thread section of the fixing element.

* * * * *

UNITED STATES PATENT AND TRADEMARK OFFICE
CERTIFICATE OF CORRECTION

| | | |
|---|---|---|
| PATENT NO. | : 8,454,658 B2 | Page 1 of 1 |
| APPLICATION NO. | : 12/822494 | |
| DATED | : June 4, 2013 | |
| INVENTOR(S) | : Stephan Lindner | |

It is certified that error appears in the above-identified patent and that said Letters Patent is hereby corrected as shown below:

In the Claims

In column 21, line 18, please delete "claim 1" and replace with --claim 18--.

Signed and Sealed this
Eleventh Day of March, 2014

Michelle K. Lee
*Deputy Director of the United States Patent and Trademark Office*